United States Patent
Da Cruz et al.

(10) Patent No.: US 11,717,258 B2
(45) Date of Patent: *Aug. 8, 2023

(54) METHODS AND SYSTEMS FOR A SHAPE-CHANGING INVASIVE DEPLOYABLE DEVICE

(71) Applicant: GE Precision Healthcare LLC, Milwaukee, WI (US)

(72) Inventors: Edouard Da Cruz, Nice (FR); Giandonato Stallone, Nice (FR); Flavien Daloz, Antibes (FR)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,282

(22) Filed: May 12, 2020

(65) Prior Publication Data
US 2021/0353253 A1 Nov. 18, 2021

(51) Int. Cl.
- *A61B 8/12* (2006.01)
- *A61B 8/00* (2006.01)
- *A61B 8/08* (2006.01)

(52) U.S. Cl.
CPC ............ *A61B 8/12* (2013.01); *A61B 8/08* (2013.01); *A61B 8/445* (2013.01); *A61B 8/4494* (2013.01)

(58) Field of Classification Search
None
See application file for complete search history.

(56) References Cited

U.S. PATENT DOCUMENTS

| | | | |
|---|---|---|---|
| 7,220,233 B2 | 5/2007 | Nita et al. | |
| 7,500,954 B2 | 3/2009 | Wilser et al. | |
| 10,405,830 B2 | 9/2019 | Garbini et al. | |
| 2005/0215895 A1* | 9/2005 | Popp | A61B 8/445 600/437 |
| 2006/0276711 A1* | 12/2006 | Yuan | A61B 8/12 600/437 |
| 2007/0066902 A1* | 3/2007 | Wilser | A61B 8/445 600/459 |
| 2008/0146937 A1 | 6/2008 | Lee et al. | |
| 2008/0287798 A1 | 11/2008 | Lee et al. | |
| 2019/0069949 A1* | 3/2019 | Vrba | A61B 17/122 |

FOREIGN PATENT DOCUMENTS

JP 5709366 B2 4/2015

OTHER PUBLICATIONS

Wildes et al. ("4-D ICE: A 2-D 4D ICE: A 2-D Array Transducer With Integrated ASIC in a 10-Fr Catheter for Real-Time 3-D Intracardiac Echocardiography"; IEEE Transactions on Ultrasonics, Ferroelectrics, and Frequency Control , vol. 63, No. 12, Dec. 2016).*

* cited by examiner

*Primary Examiner* — Shahdeep Mohammed
(74) *Attorney, Agent, or Firm* — McCoy Russell LLP

(57) ABSTRACT

Various methods and systems are provided for a deployable invasive device. In one example, the deployable invasive device has a transducer with a plurality of transducer arrays linked by at least one shape memory material, the at least one shape memory material configured to transition the transducer between a first, folded shape and a second, unfolded shape in response to one or more stimuli. When in the second, unfolded shape, an active area of the transducer is increased relative to the first, folded shape.

12 Claims, 13 Drawing Sheets

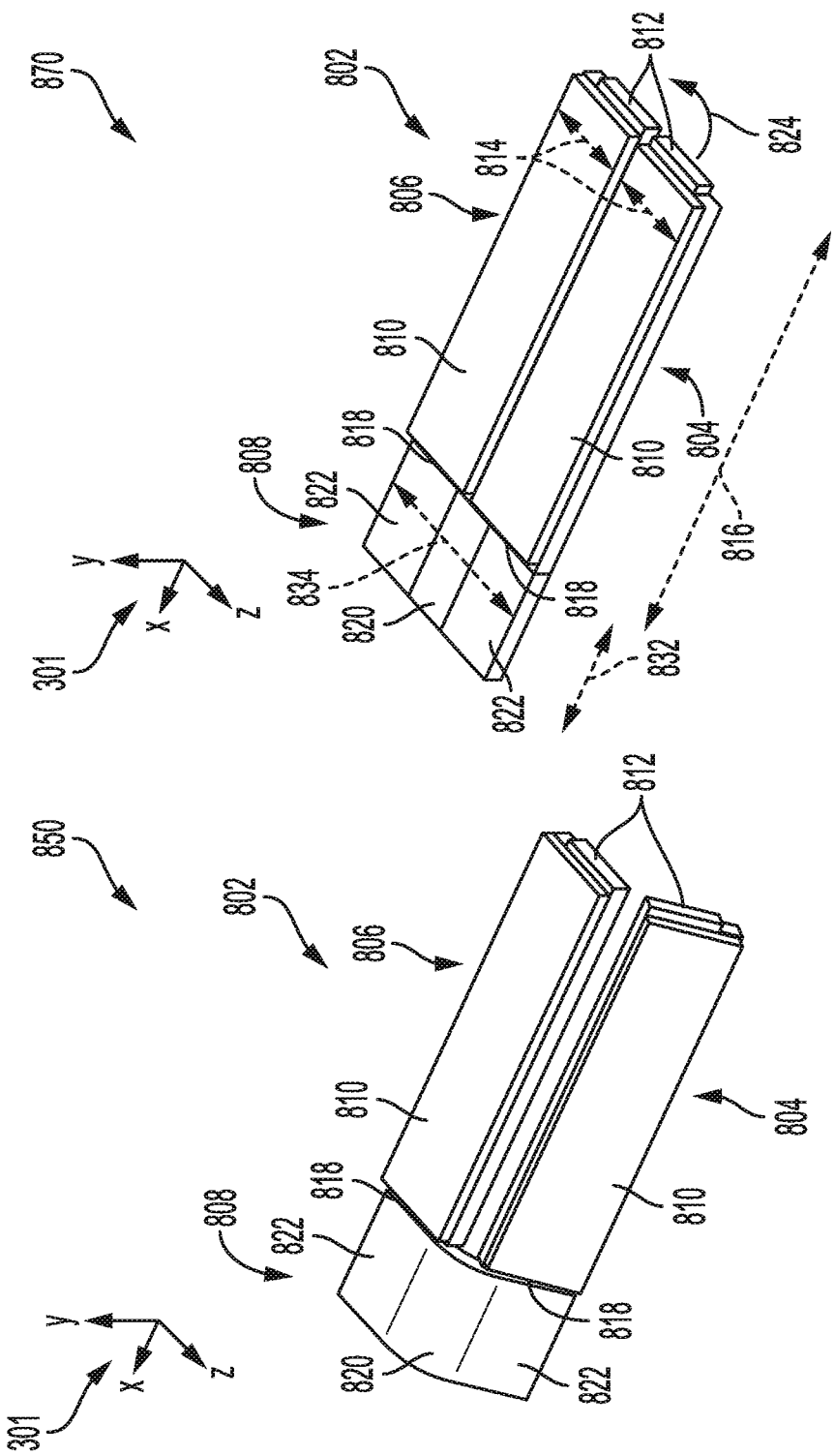

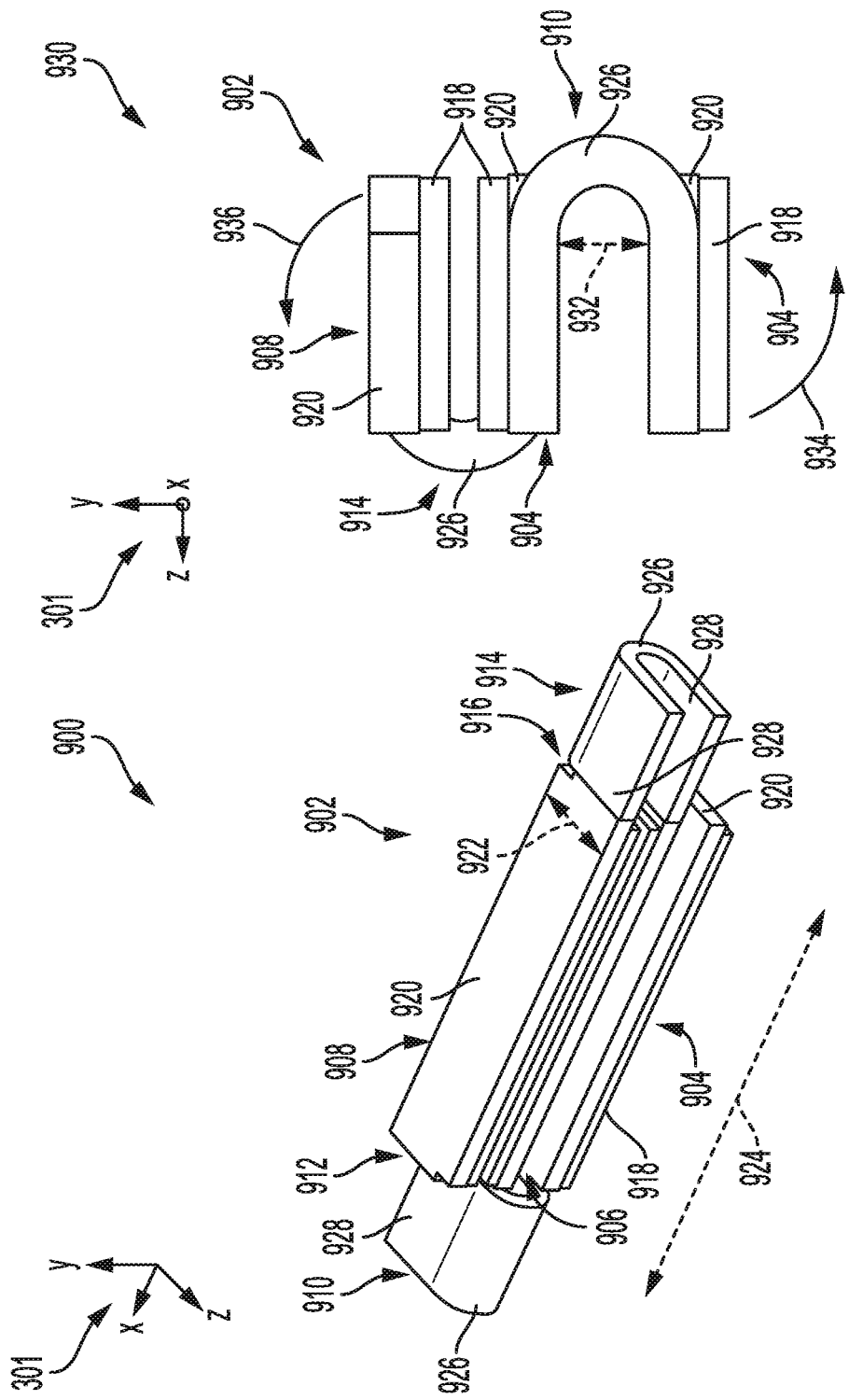

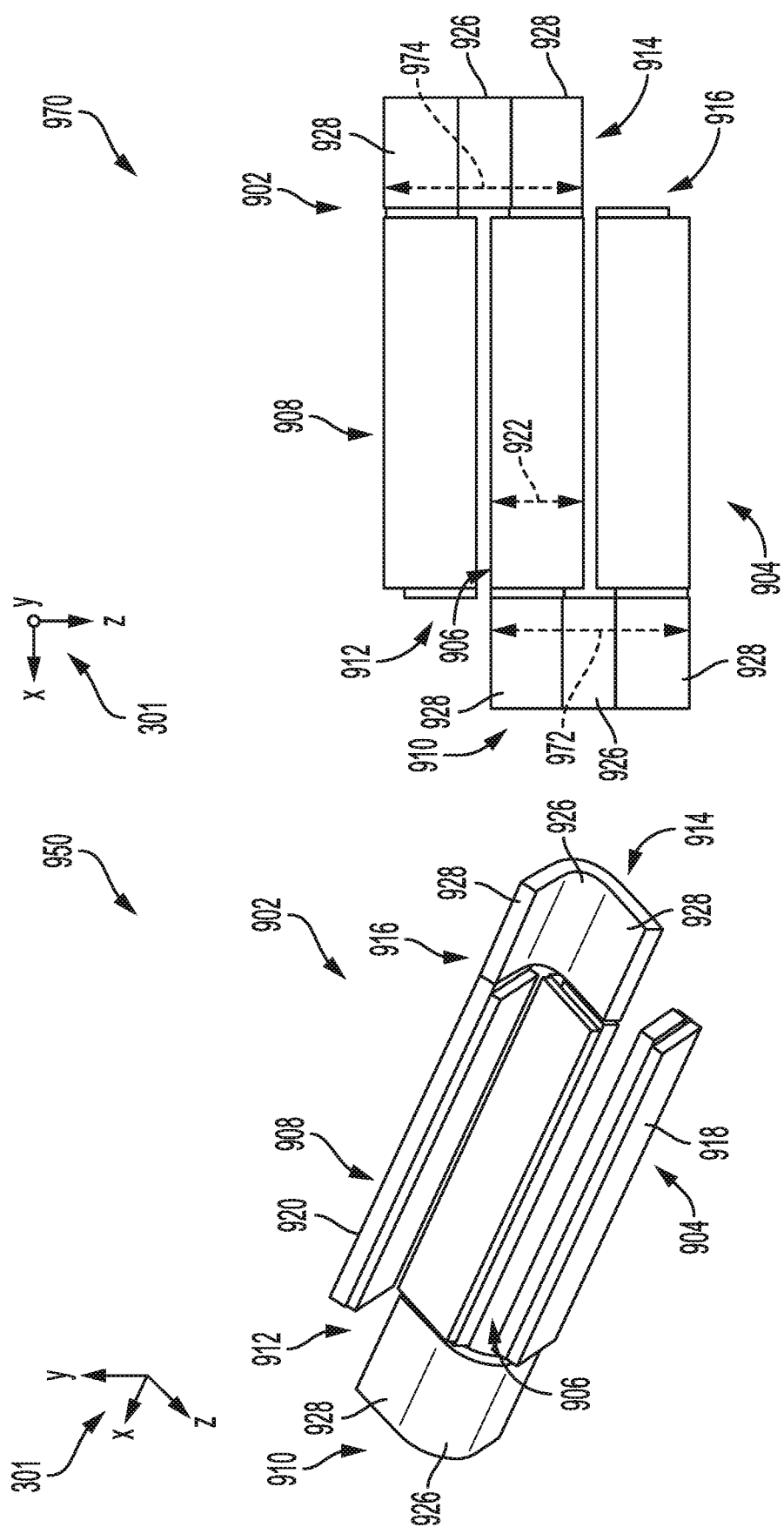

METHODS AND SYSTEMS FOR A SHAPE-CHANGING INVASIVE DEPLOYABLE DEVICE

FIELD

Embodiments of the subject matter disclosed herein relate to a deployable catheter.

BACKGROUND

Invasive devices may be used to obtain information about tissues, organs, and other anatomical regions that may be difficult to gather via external scanning or imaging techniques. An invasive device may be a deployable catheter which may be inserted intravenously into a patient's body. In one example, the device may be used for intracardiac echocardiography imaging where the device is introduced into the heart via, for example, the aorta, inferior vena cava, or jugular vein. The device may include an ultrasound probe with an aperture size conforming to dimensions that enables the device to fit through an artery or vein. Thus a resolution and penetration of the ultrasound probe may be determined by a maximum allowable diameter of the invasive device.

BRIEF DESCRIPTION

In one embodiment, a deployable invasive comprises a transducer with a plurality of transducer arrays linked by at least one shape memory material, the at least one shape memory material configured to transition the transducer between a first, folded shape and a second, unfolded shape in response to one or more stimuli, wherein in the second, unfolded shape, the plurality of transducer arrays are arranged contiguously with one another without any other transducer components positioned in a region between each of the plurality of transducer arrays, the region defined by inner edges of the plurality of transducer arrays and edges of the plurality of transducer arrays perpendicular to an azimuth direction, and an active area of the transducer is increased relative to the first, folded shape. The transducer size may thereby be reduced to allow the transducer to pass through intravenous channels and increase when desired to obtain high resolution data with increased acquisition speed.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 8C shows a perspective view of the third example of the transducer of FIG. 8A in a transitional configuration.

FIG. 8D shows a perspective view of the third example of the transducer of FIG. 8A in an unfolded configuration.

FIG. 9A shows a perspective view of a fourth example of a transducer adapted with a shape memory material in a folded configuration.

FIG. 9B shows an end view of the fourth example of the transducer of FIG. 9A.

FIG. 9C shows a perspective view of the fourth example of the transducer of FIG. 9A in a transitional configuration.

FIG. 9D shows a perspective view of the fourth example of the transducer of FIG. 9A in an unfolded configuration.

FIGS. 1-4 and 6A-9D are drawn approximately to scale although other relative dimensions may be used.

DETAILED DESCRIPTION

Figure 1:
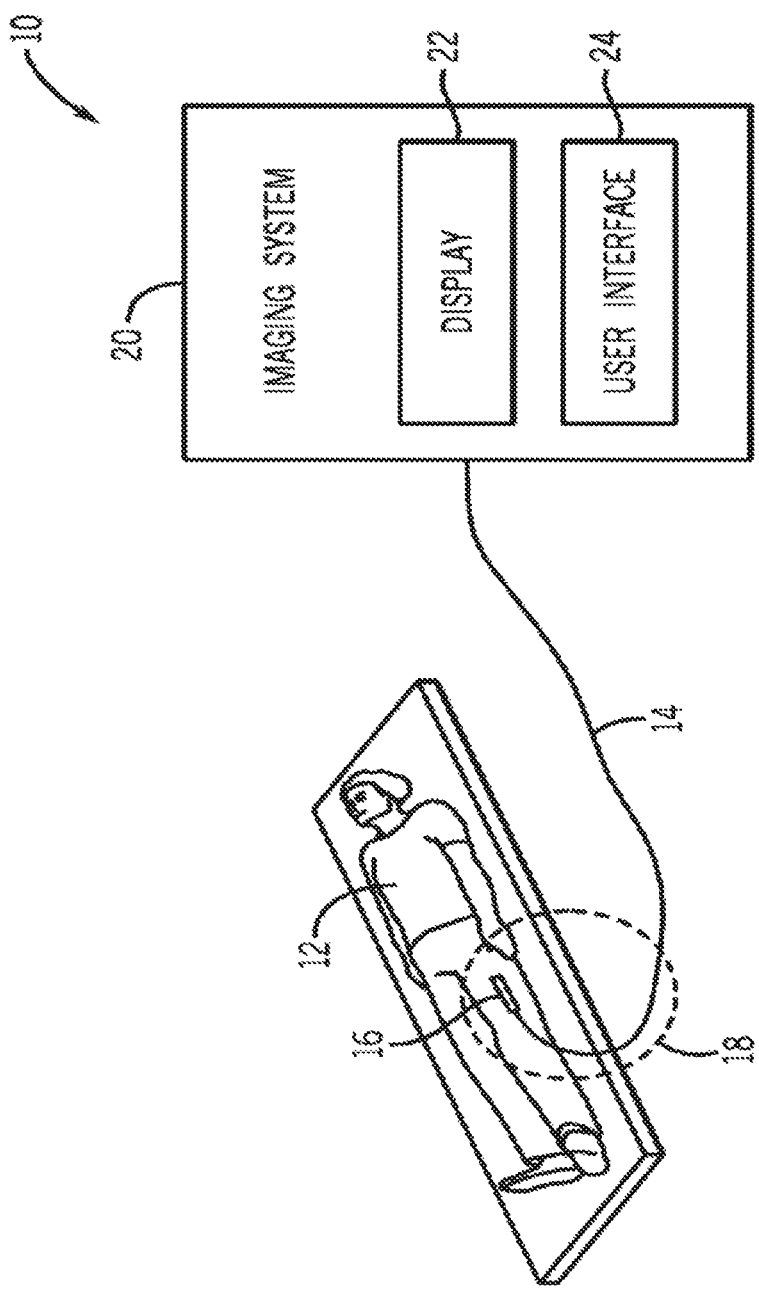
FIG. 1 shows a block diagram of an exemplary imaging system including a deployable catheter.
Figure 2:
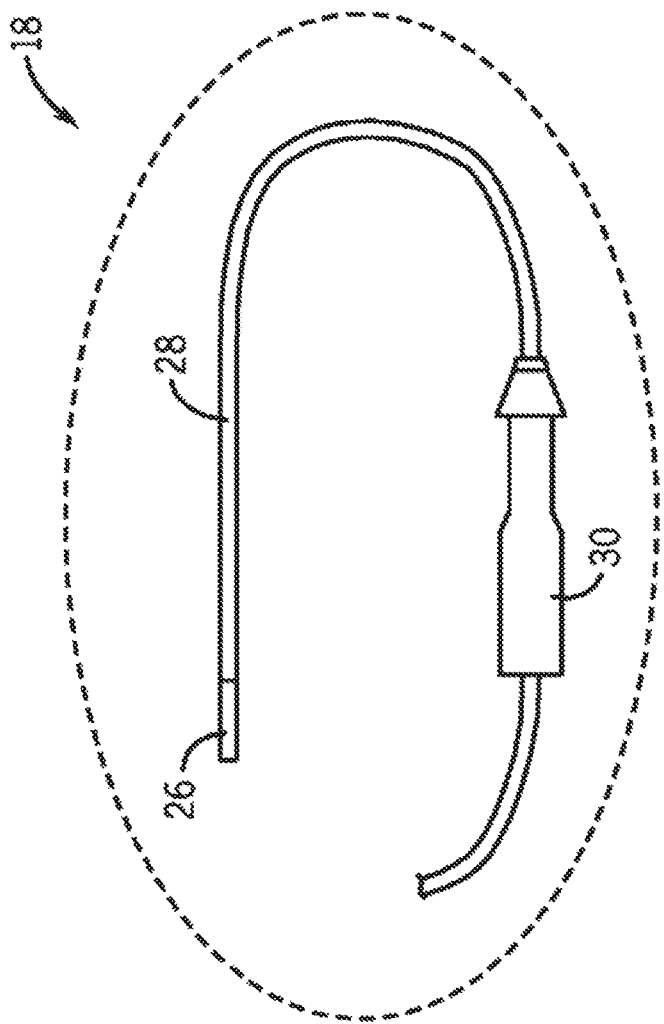
FIG. 2 shows the deployable catheter of FIG. 1 in greater detail, including an exemplary imaging catheter tip and transducer for use in the system illustrated in FIG. 1.
Figure 10:
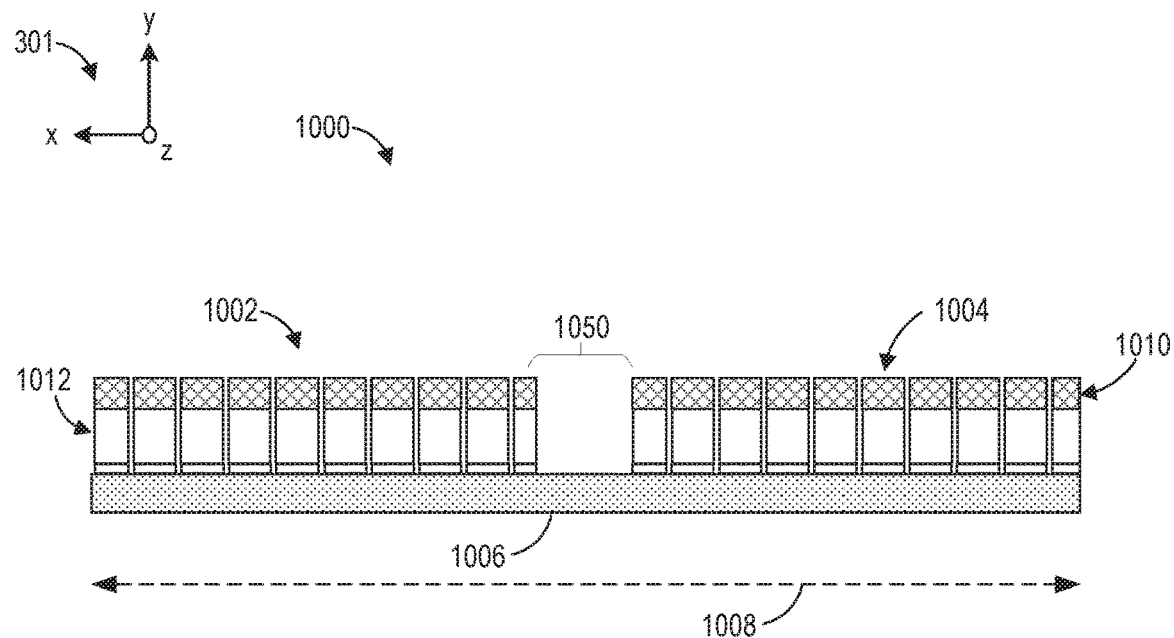
FIG. 10 shows a fifth example of a transducer adapted with a shape memory material forming an acoustic layer of the transducer.
Figure 11:
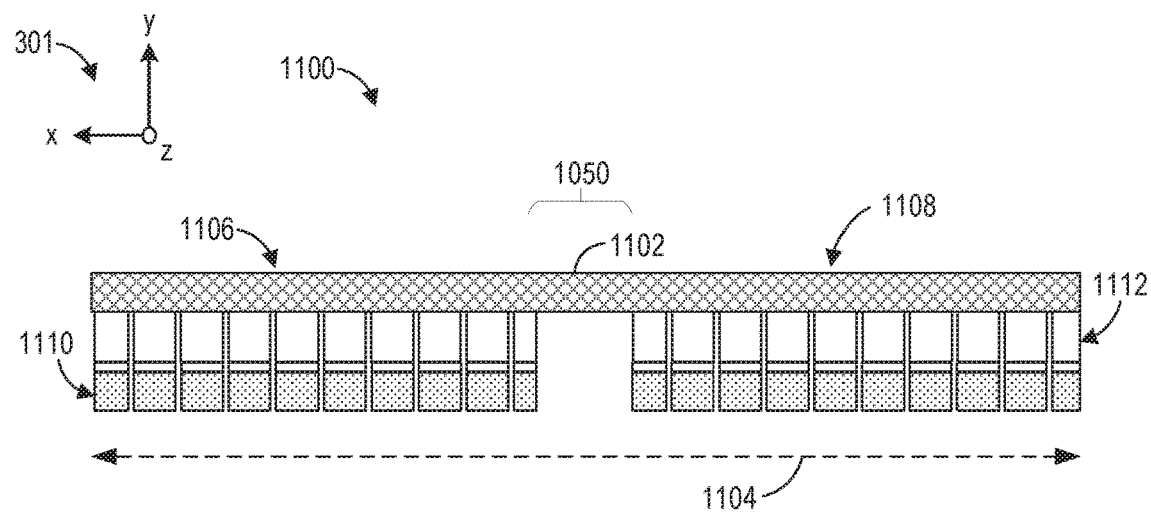
FIG. 11 shows a sixth example of a transducer adapted with a shape memory material forming an acoustic layer of the transducer.
Figure 12:
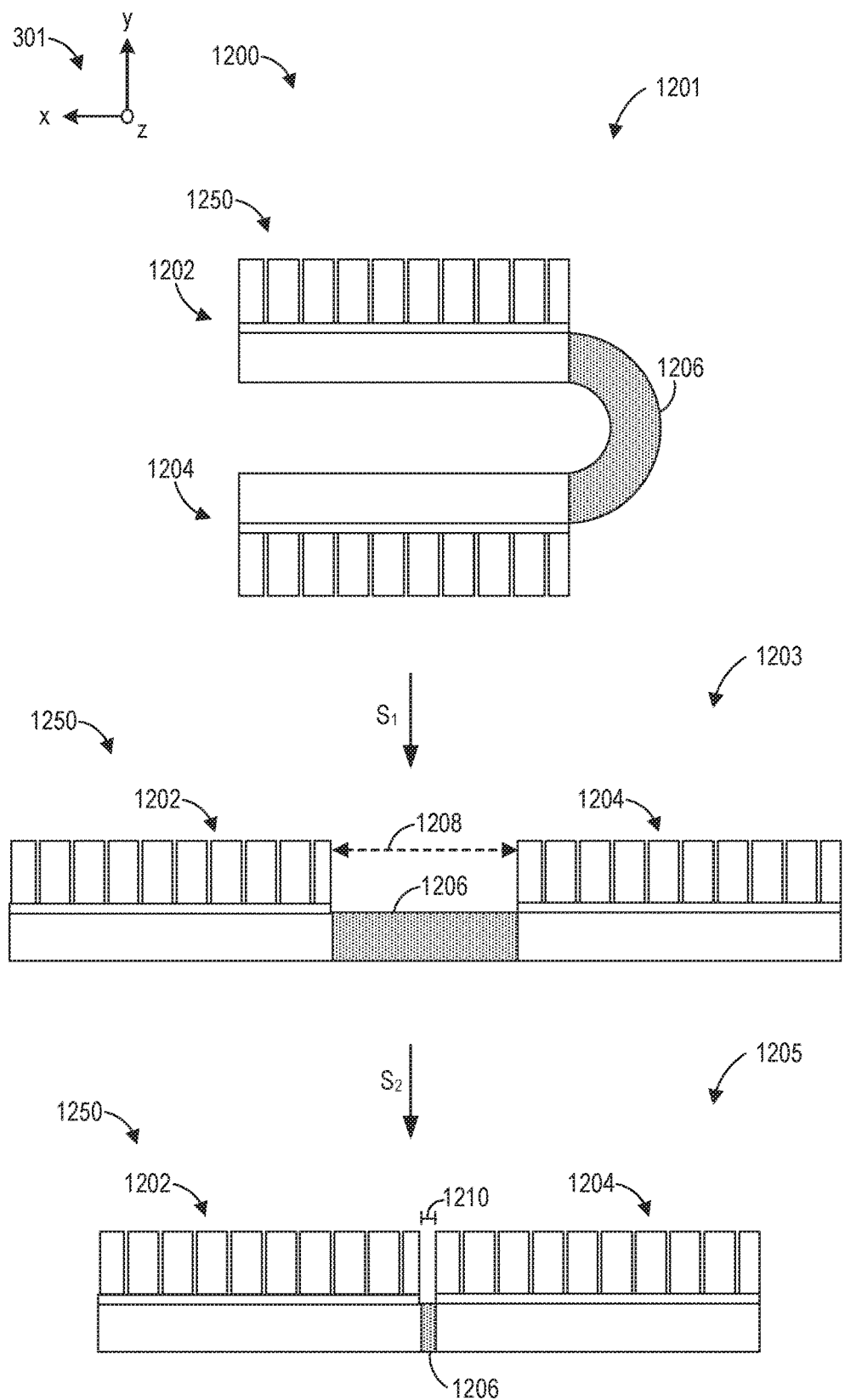
FIG. 12 is a diagram illustrating a shape transition mode variation of a shape memory material implemented in a transducer.

The following description relates to various embodiments of a deployable invasive device. The deployable invasive device may be a deployable catheter in an imaging system and configured to be inserted into a patient to obtain information about internal tissues and organs. An example of an imaging system equipped with a deployable catheter is shown in FIG. 1. A side view of the deployable catheter is depicted in FIG. 2 and inner components of the deployable catheter are illustrated in a first cross-sectional view of the deployable catheter in FIG. 3. A second cross-sectional view of the deployable catheter is shown as a schematic in FIG. 4. Transitioning of a transducer adapted with a shape memory material, which may be included in the deployable catheter, between a first shape and a second shape is shown in FIG. 5. Examples of transducer incorporating the shape memory material in various locations relative to an active area of the transducer and with the transducer in different configurations are shown in FIGS. 6A-11. For example, the shape memory material may be arranged between transducer arrays, as shown in FIGS. 6A-7B, outside of the active area, as shown in FIGS. 8A-9D, or incorporated as an acoustic layer in the transducer, as shown in FIGS. 10-11. An additional mode of shape transition of the shape memory material is depicted in FIG. 12, the additional mode including contraction of the shape memory material along at least one dimension.

FIGS. 1-12 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Medical imaging techniques, such as ultrasound imaging, may be used to obtain real-time data about a patient's tissues, organs, blood flow, etc. However, high resolution data for inner cavities of the tissues and organs may be difficult to obtain via external scanning of the patient. In such instances, a deployable catheter outfitted with a probe may be inserted intravenously into the patient and directed to a target site. The deployable catheter may travel through a narrow channel, such as a vein or artery and therefore may have a similar diameter. However, the narrow diameter of the deployable catheter may limit a size of the probe which, in turn, may constrain data quality and acquisition speed provided by the probe. For example, when the probe is an ultrasound probe, a resolution and penetration of the ultrasound probe may be determined by a size of a transducer of the probe. In order to increase a quality of images generated by the ultrasound probe a larger transducer than can be enclosed within a housing of the deployable catheter may be demanded.

In one example, the issues described above may be at least partially addressed by incorporating a shape memory material into the deployable catheter. The shape memory material may be a shape memory polymer (SMP) configured to alternate between at least two different shapes. A footprint of a transducer of the deployable catheter, where the SMP is coupled to the transducer, may be selectively increased or decreased. The shape-changing behavior of the SMP allows the transducer to have, for example, a first shape with a first set of dimensions enabling the transducer array to be readily inserted into the patient's body within the deployable catheter housing. In response to exposure to a stimulus, the SMP may adjust to a second shape with a second set of dimensions that increases a size of the transducer.

The SMP may be coupled to the transducer via more than one configuration, allowing flexibility in a design of the transducer to accommodate available packaging space and to enhance a performance of the transducer. For example, a positioning of the SMP relative to an active area of the transducer may be varied and/or the SMP may be configured to change shape via more than one mode. In this way, the imaging probe may be in a conformation more favorable for intravenous passage within the patient and subsequently enlarged when deployed in a target anatomical region to obtain high resolution data. By leveraging the SMP to induce shape transitions, a cost of the deployable catheter may be maintained low while allowing for a large range of deformation.

Turning now to FIG. 1, a block diagram of an exemplary system 10 for use in medical imaging is illustrated. It will be appreciated that while described as an ultrasound imaging system herein, the system 10 is a non-limiting example of an imaging system which may utilize a deployable device to obtain medical images. Other examples may include incorporating other types of invasive probes such as endoscopes, laparoscopes, surgical probes, intracavity probes, amongst others. The system 10 may be configured to facilitate acquisition of ultrasound image data from a patient 12 via an imaging catheter 14. For example, the imaging catheter 14 may be configured to acquire ultrasound image data representative of a region of interest in the patient 12 such as the cardiac or pulmonary region. In one example, the imaging catheter 14 may be configured to function as an invasive probe. Reference numeral 16 is representative of a portion of the imaging catheter 14 disposed inside the patient 12, such as inserted into a vein. Reference numeral 18 is indicative of a portion of the imaging catheter 14 depicted in greater detail in FIG. 2.

The system 10 may also include an ultrasound imaging system 20 that is in operative association with the imaging catheter 14 and configured to facilitate acquisition of ultrasound image data. It should be noted that although the exemplary embodiments illustrated hereinafter are described in the context of a medical imaging system, such as an ultrasound imaging system, other imaging systems and applications are also contemplated (e.g., industrial applications, such as nondestructive testing, borescopes, and other applications where ultrasound imaging within confined spaces may be used). Further, the ultrasound imaging system 20 may be configured to display an image representative of a current position of the imaging catheter tip within the patient 12. As illustrated in FIG. 1, the ultrasound imaging system 20 may include a display area 22 and a user interface area 24. In some examples, the display area 22 of the ultrasound imaging system 20 may be configured to display a two- or three-dimensional image generated by the ultrasound imaging system 20 based on the image data acquired via the imaging catheter 14. For example, the display area 22 may be a suitable CRT or LCD display on which ultrasound images may be viewed. The user interface area 24 may include an operator interface device configured to aid the operator in identifying a region of interest to be imaged. The operator interface may include a keyboard, mouse, trackball, joystick, touch screen, or any other suitable interface device.

FIG. 2 illustrates an enlarged view of the portion 18 shown in FIG. 1 of the imaging catheter 14. As depicted in FIG. 2, the imaging catheter 14 may include a tip 26 on a distal end of a flexible shaft 28. The catheter tip 26 may house a transducer and motor assembly. The transducer may include one or more transducer array, each transducer array including one or more transducer elements. The imaging catheter 14 may also include a handle 30 configured to facilitate an operator manipulating the flexible shaft 28.

Figure 3:
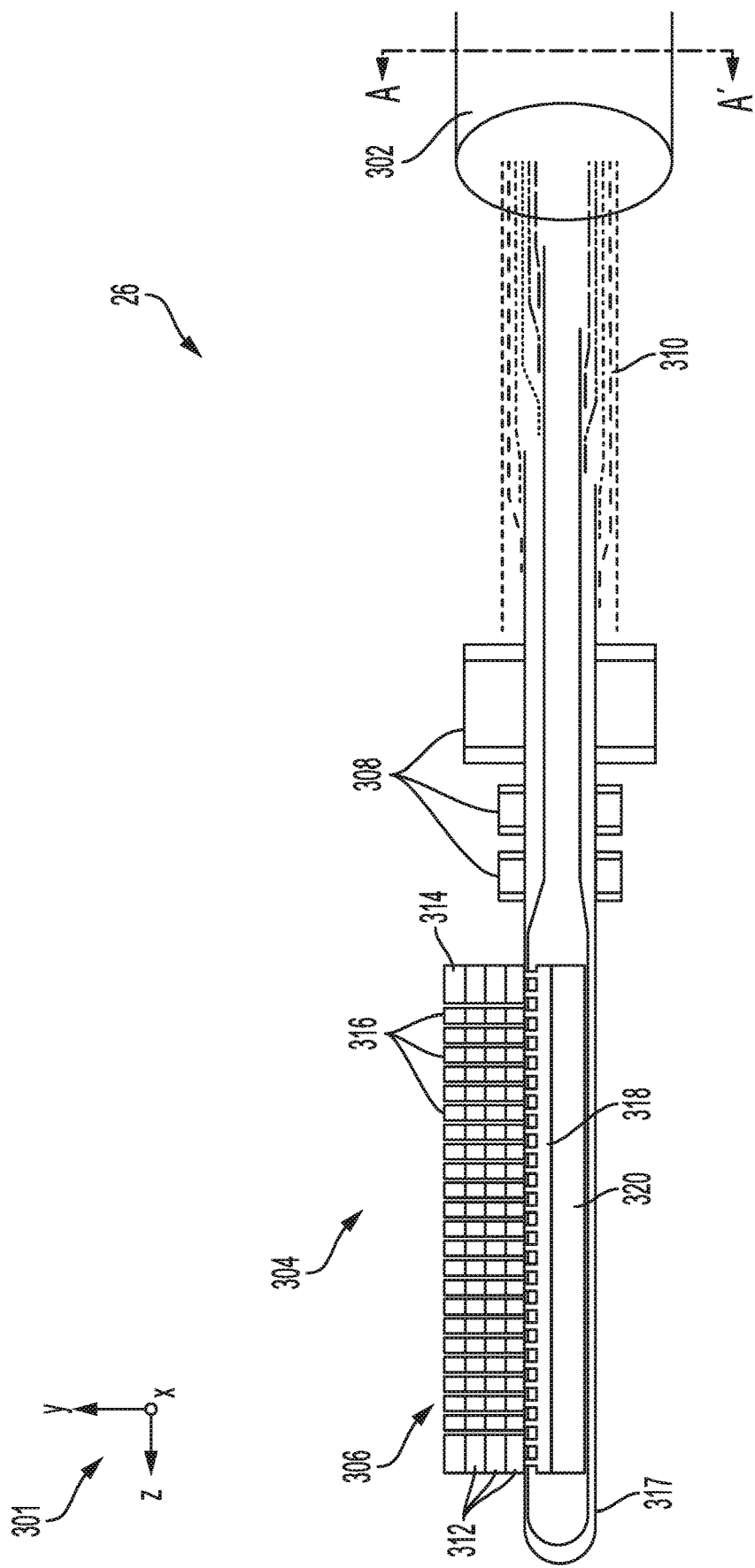
FIG. 3 shows a first cross-sectional view of the exemplary imaging catheter tip which may be included in the deployable catheter of FIG. 2.

An example of the catheter tip 26 of FIG. 2 is shown in FIG. 3. A set of reference axes 301 are provided, indicating a y-axis, an x-axis, and a z-axis. The catheter tip 26 may have a housing 302 surrounding a transducer 304 which may include at least one transducer array 306, capacitors 308, and a catheter cable 310. The other components not shown in FIG. 3 may also be enclosed within the housing 302, such as a motor, a motor holder, a thermistor, and an optional lens, for example. Furthermore, in some examples, the catheter tip 26 may include a system for filling the tip with a fluid, such as an acoustic coupling fluid.

The transducer array 306 has several layers stacked along the y-axis and extending along the x-z plane. One or more layers of the transducer array 306 may be layers of transducer elements 312. In one example, the transducer elements 312 may be piezoelectric elements, where each piezoelectric element may be a block formed of a natural material such as quartz, or a synthetic material, such as lead zirconate titanate, that deforms and vibrates when a voltage is applied by, for example, a transmitter. In some examples, the piezoelectric element may be a single crystal with crystallographic axes, such as lithium niobate and PMN-PT ($Pb(Mg_{1/3}Nb_{2/3})O_3$—$PbTiO_3$). The vibration of the piezoelectric element generates an ultrasonic signal formed of ultrasonic waves that are transmitted out of the catheter tip 26. The piezoelectric element may also receive ultrasonic waves, such as ultrasonic waves reflected from a target object, and convert the ultrasonic waves to a voltage. The voltage may be transmitted to a receiver of the imaging system and processed into an image.

An acoustic matching layer 314 may be positioned above the transducer elements 312. The acoustic matching layer 314 may be a material positioned between the transducer elements 312 and a target object to be imaged. By arranging the acoustic matching layer 314 in between, the ultrasonic waves may first pass through the acoustic matching layer 314, and emerge from the acoustic matching layer 314 in phase, thereby reducing a likelihood of reflection at the target object. The acoustic matching layer 314 may shorten a pulse length of the ultrasonic signal, thereby increasing an axial resolution of the signal.

The layers formed by the acoustic matching layer 314 and the transducer elements 312 may be diced along at least one of the y-x plane and the y-z plane to form individual acoustic stacks 316. Each of the acoustic stacks 316 may be electrically insulated from adjacent transducers but may all be coupled to common layers positioned below or above the transducer elements, with respect to the y-axis.

An electrical circuit 318 may be layered below, relative to the y-axis, the transducer elements 312. In one example, the electrical circuit may be at least one application-specific integrated circuit (ASIC) 318 directly in contact with each of the acoustic stacks 316. Each ASIC 318 may be coupled to one or more flex circuits 317 which may extend continuously between the transducer array 306 and the catheter cable 310. The flex circuits 317 may be electrically coupled to the catheter cable 310 to enable transmission of electrical signals between the transducer array 306 and an imaging system, e.g., the imaging system 20 of FIG. 1. The electrical signals may be tuned by the capacitors 308 during transmission.

An acoustic backing layer 320 may be arranged below the ASIC 318, with respect to the z-axis. In some examples, as shown in FIG. 3, the backing layer 320 may be a continuous layer of material that extends along the x-z plane. The backing layer 320 may be configured to absorb and attenuate backscattered waves from the transducer elements 312. A bandwidth of an acoustic signal generated by the transducer elements 312, as well as the axial resolution, may be increased by the backing layer 320.

As described above, the transducer 304, the capacitors 308, and the catheter cable 310 may be enclosed within the housing 302. Thus a size, e.g., a diameter or width of the components may be determined by an inner diameter of the housing 302. An inner diameter of the housing 302 may be, in turn, determined by an outer diameter and a desirable thickness of the housing 302. The outer diameter of the housing 302 may be constrained by a region of a patient's body through which the imaging catheter is inserted. For example, the imaging catheter may be an intracardiac echocardiography (ICE) catheter used to obtain images of cardiac structures and blood flow inside the patient's heart.

The imaging catheter may be introduced into the heart through the aorta, inferior vena cava, or jugular vein. In some instances, the imaging catheter may be fed through regions with narrower diameters, such as the coronary sinus, the tricuspid valve, and the pulmonary artery. As such, the outer diameter of the imaging catheter may not be greater than 10 Fr or 3.33 mm. The outer diameter and corresponding inner diameter of the imaging catheter housing are shown in FIG. 4 in a cross-section 400 of the housing 302 of the catheter tip 26, taken along line A-A' depicted in FIG. 3.

Figure 4:
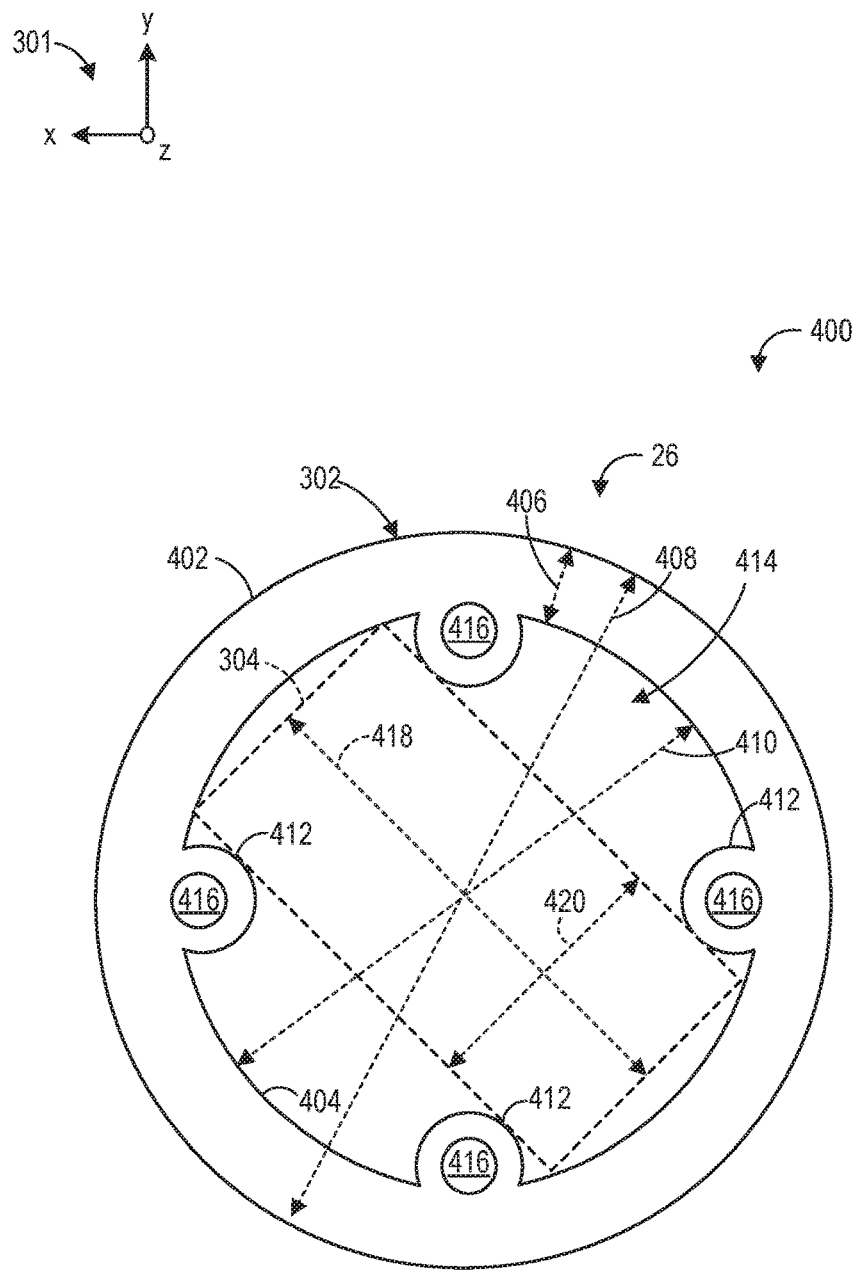
FIG. 4 is a schematic of a second cross-sectional view of the deployable catheter of FIG. 2.
Figure 5:
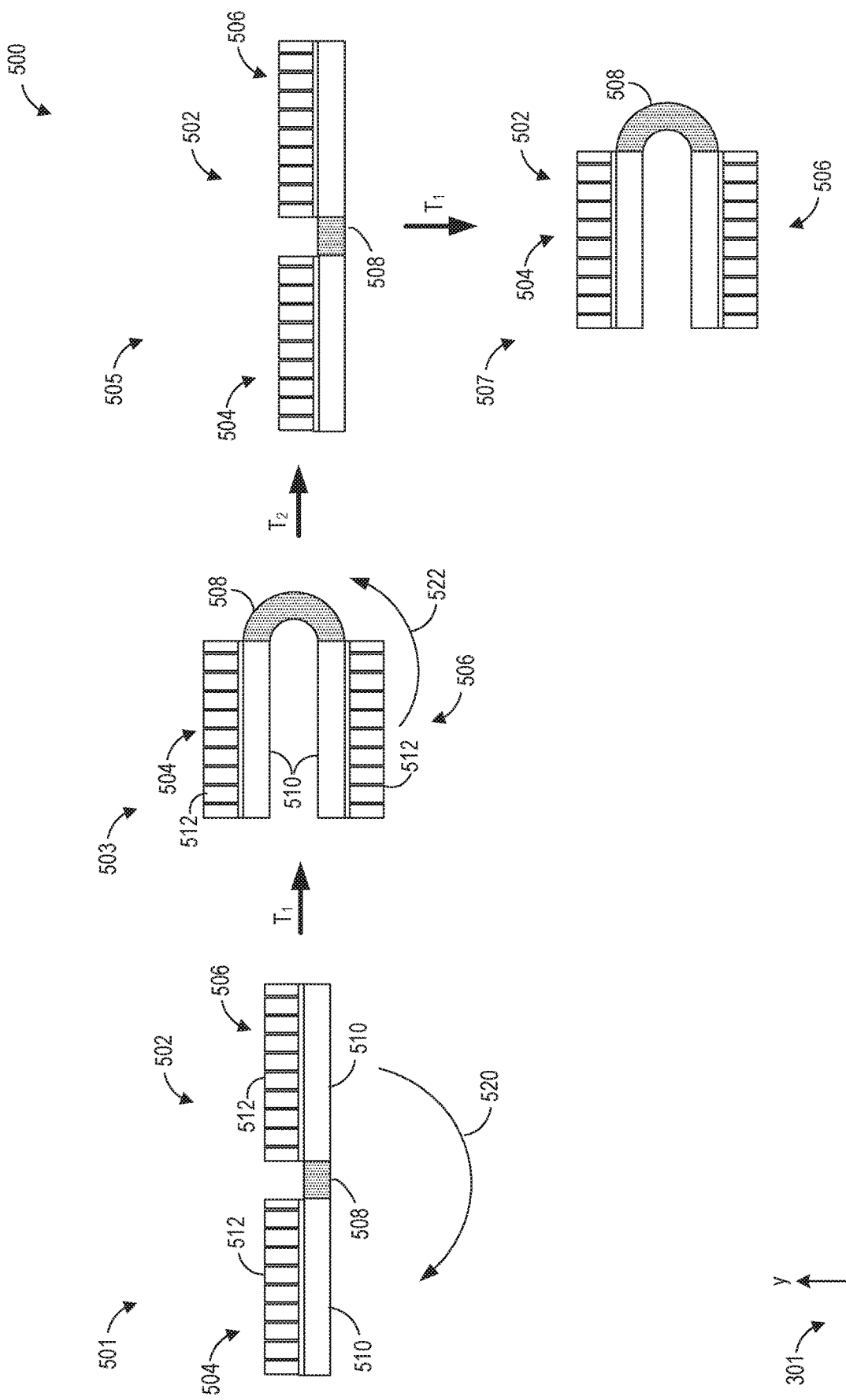
FIG. 5 is a first diagram showing a two-way shape memory effect of a transducer incorporating a shape memory material.

As shown in FIG. 4, an outer surface 402 of the housing 302 of the imaging catheter may be spaced away from an inner surface 404 of the housing 302 by a thickness 406 of the housing 302. The thickness 406 of the housing 302 may be optimized to provide the housing 302 with a target degree of structural stability, e.g. resistance to deformation, balanced with flexibility, e.g., ability to bend when a force is applied. In one example, an outer diameter 408 of the housing 302 may be 3.33 mm, the thickness 406 may be 0.71 mm, and an inner diameter 410 of the housing 302 may be 2.62 mm. In other examples, the outer diameter of the housing may be between 2-5 mm, the thickness may be between 0.24-1 mm, and the inner diameter may be between 1-4 mm. In yet other examples, the imaging catheter may have a variety of dimensions, depending on application. For example, an endoscope may have an outer diameter 10-12 mm. It will be appreciated that the imaging catheter may have various diameters and sizes without departing from the scope of the present disclosure.

The inner surface 404 of the housing 302 may include lobes 412 protruding into an inner volume, or lumen 414 of the housing 302. The lobes 412 may be semi-circular projections, each enclosing an individual lumen 416 for housing a steering wire of the imaging catheter. An arrangement of a transducer 304 of the imaging catheter within the lumen 414 of the housing 302 is indicated by a dashed rectangle. A maximum elevation aperture 418 of the transducer 304 may be determined based on the inner diameter 410 of the housing 302 and a height 420 of the transducer 304 may be configured to fit between the lobes 412 of the housing 302. In one example, the elevation aperture 418 may be a maximum of 2.5 mm and the height 420 may be a maximum of 1 mm.

As described above, dimensions of the transducer 304 may be determined by the inner diameter 410, thickness 406, and outer diameter 408 of the housing 302 which may, in turn, be determined based on insertion of the imaging catheter into specific regions of the patient's anatomy. The constraints imposed on a size of the transducer 304 and diameter 422 of the catheter cable 310, may affect a resolution, penetration, and fabrication of the transducer 304. Each of the resolution, penetration and ease of fabrication may be enhanced by increasing the size of the transducer 304 but the geometry of the transducer 304, and therefore performance, is bound by the dimensions of the catheter housing 302 in order for the deployable catheter to travel intravenously through a patient.

In one example, the transducer may be enlarged upon deployment at a target site by adapting the transducer with a shape memory material. The shape memory material may be a shape memory polymer (SMP) configured to respond mechanically to one or more stimuli. Examples of SMPs include linear block copolymers, such as polyurethanes, polyethylene terephthalate, polyethyleneoxide, and other thermoplastic polymers such as polynorbornene. In one example, the SMP may be a powder mixture of silicone and tungsten in an acrylic resin. The SMP may be stimulated by physical stimuli, such as temperature, moisture, light, magnetic energy, electricity, etc., by chemical stimuli, such as chemicals, pH level, etc., and by biological stimuli, such as presence of glucose and enzymes. When applied to an imaging catheter, the transducer may incorporate the SMP to enable a shape of the transducer to be altered upon exposure to at least one stimulus. The SMP may have physical properties as provided below in Table 1 which may offer more desirable characteristics than other types of shape memory materials, such as shape memory alloys. For example, SMPs may have a higher capacity for elastic deformation, lower cost, lower density, as well as greater biocompatibility and biodegradability. In particular, the lower cost of SMPs may be desirable for application in disposable deployable catheters.

TABLE 1

Physical Properties of Shape Memory Polymers

| Property | Range |
| --- | --- |
| Density (g/cm³) | 0.2-3 |
| Extent of deformation | Up to 800% |
| Required stress for deformation (MPa) | 1-3 |
| Stress generated upon recovery (MPa) | 1-3 |
| Transition temperature (° C.) | −10 to 100 |
| Recovery speed | 1 s to 1 HR |
| Processing condition | <200° C.; low pressure |
| Cost | <$10/lb |

In one example, the SMP may have two-way shape memory so that the SMP may adjust between two shapes without demanding reprogramming or application of an external force. For example, the SMP may convert to a temporary shape in response to a first stimulus and revert to a permanent shape in response to a second stimulus. The first and second stimuli may be of a same or different type, e.g., the first stimulus may be a high temperature and the second stimulus may be a low temperature or the first stimulus may be a humidity level and the second stimulus may be a threshold temperature. The two-way shape memory behavior is neither mechanically nor structurally constrained, thereby allowing the SMP to switch between the temporary shape and permanent shape without applying the external force.

As an example, conversion of a transducer 502 between a first shape and a second shape is shown in a first diagram 500 in FIG. 5. The transducer 502 includes a first transducer array 504 and a second transducer array 506 where the second transducer array 506 is aligned with the first transducer array 504 along the z-axis and spaced away from the first transducer array 504. In other words, the transducer 502 has an overall planar shape with the first and second transducer arrays 504, 506 co-planar with one another along a common plane, e.g., the x-z plane. A first step 501 of the first diagram 500, depicts coupling of an SMP 508 to a backing layer 510 of each of the first and second transducer arrays 504, 506. The SMP 508, configured as a two-way memory SMP, is arranged between the transducer arrays along the z-axis and may be fixedly attached to edges of the backing layers 510 and arranged co-planar with the backing layers 510. For example, the backing layers 510 and the SMP 508 arranged therebetween may form a continuous, planar unit. Transducer elements 512 are laminated onto the backing layer 510 of the first and second transducer arrays 504, 506.

In some examples, the SMP 508 may form a continuous layer entirely across the transducer 502. The SMP 508 may, for example, be an acoustic layer of the transducer 502, such as a matching layer or a backing layer. By incorporating the SMP 508 as an acoustic layer, an assembly and number of components of the transducer may be simplified without adversely affecting a reduction in size of the transducer footprint. Implementing the SMP as an acoustic layer of the transducer is discussed further below, with reference to FIGS. 10-11.

The transducer 502 is exposed to a first temperature, $T_1$, and, at a second step 503, the SMP 508 changes shape in response to $T_1$. The SMP 508 may bend into a semi-circular shape, pivoting the second transducer array 506 substantially through 180 degrees along a first rotational direction, e.g., clockwise, as indicated by arrow 520. Bending, as referred to herein, may be any transitioning of a planar structure to a non-planar conformation. As such, various deformations of the structure from a configuration that is aligned with a plane may be considered bending.

When the SMP 508 bends, the transducer 502 may therefore also bend. While the SMP may bend through a range of angles, bending of the SMP so that two regions of the transducer 502 become stacked over one another and substantially parallel with one another is referred to as folding herein. The SMP, in some examples, may not bend to an extent that the transducer is folded. However, folding of the transducer may provide a most compact conformation of the transducer to enable passage of the deployable catheter through intravenous passages.

As a result of the folding of the transducer 502, the second transducer array 506 is positioned under the first transducer array 504, with respect to the y-axis, in a folded shape. An overall surface area of the transducer elements 512, including the transducer elements 512 of both the first and second transducer arrays 504, 506, is reduced at the second step 503 compared to the first step 501 when viewing the transducer 502 along the y-axis.

The transducer 502 is exposed to a second temperature, $T_2$, and, in response, the SMP 508 reverts to the planar geometry of the first step 501 at a third step 505 of the first diagram 500. The second transducer array 506 is pivoted substantially through 180 degrees along a second rotational direction, opposite of the first rotational direction, e.g., counterclockwise. The second temperature $T_2$ may be a higher or lower temperature than $T_1$. Subjecting the transducer 502 to $T_1$ again compels the SMP 508 to bend, folding the transducer 502 so that the second transducer array 506 is pivoted 180 degrees at a fourth step 507.

As described above, the transducer 502 may be enclosed within a housing at a tip of a deployable catheter, such as the housing 302 of FIGS. 3 and 4. To accommodate unfolding of the transducer 502 to the planar geometry, the housing may be formed of a flexible, elastic material that stretches and deforms as the transducer 502 changes shape. For example, the deployable catheter may be a balloon catheter and the housing at the catheter tip may be an inflatable balloon. The balloon may be formed from a material such as polyester, polyurethane, silicone, etc. and may be inflated by filling the balloon with a fluid or a gas. Prior to adjustment of the transducer 502 to the planar geometry, the balloon may be inflated to allow the transducer 502 to transition without impediment. Upon adjustment of the transducer 502 to the folded conformation, the balloon may be deflated by venting or draining the gas or fluid.

The steps shown in the first diagram 500 may be repeated many times. For example, prior to insertion of an imaging catheter adapted with the transducer 502 of FIG. 5 in to a patient, the transducer 502 may be initially exposed to $T_1$ to fold and decrease the size of the transducer 502. The folded transducer 502, may fit within a housing of the imaging catheter and inserted intravenously into the patient. When the transducer 502 reaches a target site within the patient, the transducer 502 may be unfolded and enlarged by subjecting the array to $T_2$. Images may be obtained while the transducer 502 is unfolded and increased in size. For example, unfolding the transducer 502 may increase an elevation aperture of the transducer 502.

When scanning is complete, the transducer 502 may be exposed again to $T_1$ to cause the transducer 502 to fold and decrease in size. The imaging catheter may then be withdrawn from the site and removed from the patient or deployed to another site for imaging within the patient. Thus the shape and size of the transducer 502 may be adjusted between the planar and folded configurations numerous times during an imaging session.

It will be appreciated that the configurations of the transducer 502 shown in FIG. 5 are non-limiting examples of shapes that the transducer may transition between. Other examples may include the transducer 502 being in a non-planar geometry at the first step 501, such as slightly bent or curved shape, becoming more bent or curved at the second step 503, and alternating between the less bent/curved and more bent/curved shapes upon exposure to one or more stimuli. In addition, the transducer 502 may fold so that the first and second transducer arrays 504, 506, are not parallel with one another. In yet other examples, the first and second transducer arrays 504, 506 may be different sizes.

Furthermore, when the SMP 508 forms an entire layer across the transducer 502, rather than forming a section between the backing layers 510 of the first and second transducer arrays 504, 506, the SMP 508 may be adapted to change shape only in an area between the transducer arrays. In one example the SMP 508 may be able to change shape via more than one type of transition. For example, the SMP 508 may bend upon exposure to one type of stimulus and shrink upon exposure to another type of stimulus. In another example, the SMP 508 may include more than one type of shape memory material. As an example, the SMP 508 may be formed of a first type of material configured to bend and a second type of material configured to shrink. Other variations in shape transitions, combination of materials, and positioning of the SMP 508 within the transducers have been contemplated.

While temperature changes are described as a stimulus for inducing changes in the SMP shape for the first diagram 500 of FIG. 5, it will be appreciated that the first diagram 500 is a non-limiting example of how deformation of the SMP may be triggered. Other types of stimuli, such as humidity, pH, UV light, etc. may be used to induce mechanical changes in the SMP. More than one type of stimulus may be applied to the SMP to achieve similar or different shape modification. Furthermore, deformation of the SMP may include other manners of shape change other than bending. For example, the SMP may curl into a jellyroll configuration or shrink along at least one dimension. Details of the mechanical deformation are described further below.

Figure 6B:
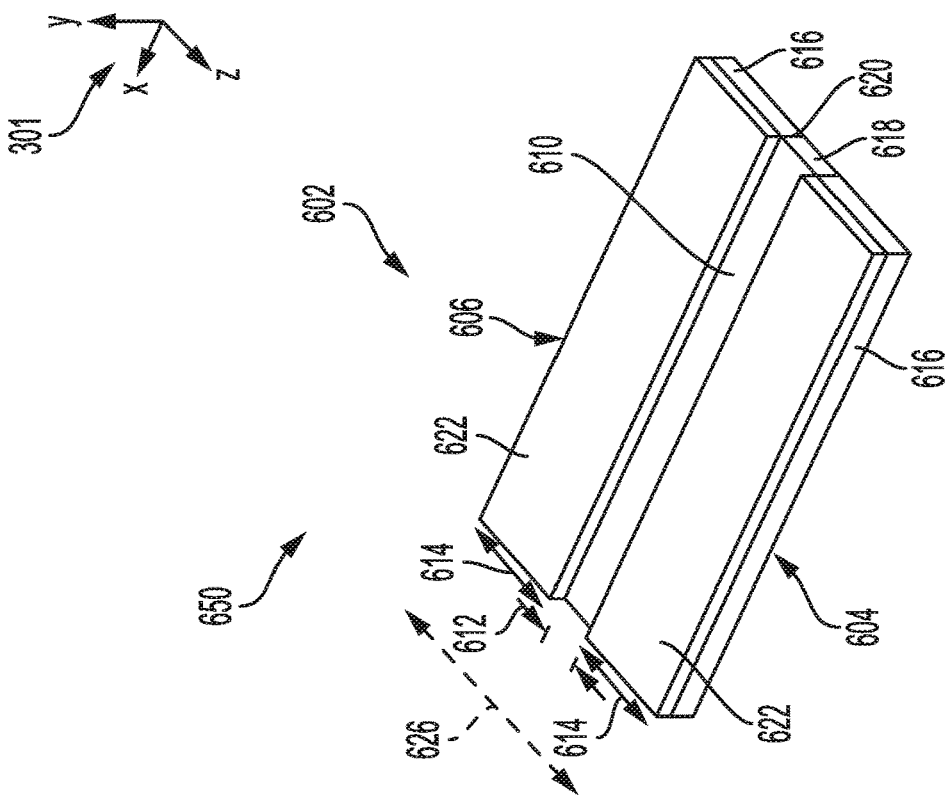
FIG. 6B shows the first example of the transducer of FIG. 6A in an unfolded configuration.
Figure 6A:
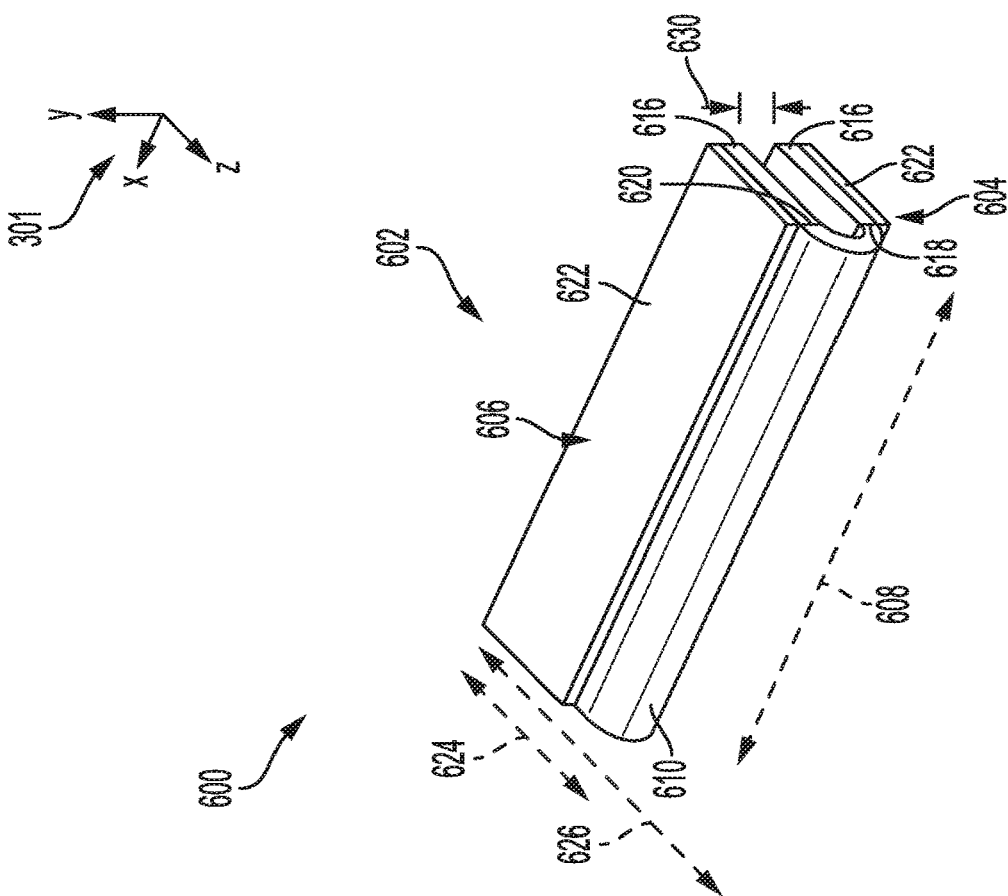
FIG. 6A shows a first example of a transducer adapted with a shape memory material in a folded configuration.

In some examples, as shown in FIG. 5, a transducer of a deployable catheter may include two sections, or two transducer arrays. Each transducer array may include one or more acoustic stacks, including, as described above with reference to FIG. 2, a matching layer, an element, and a backing layer. An ASIC may be coupled to each transducer array. A first example of a transducer 602 incorporating a SMP to enable modification of an active area of the transducer 602 is shown in FIGS. 6A and 6B. The transducer 602 is shown in a first, folded configuration 600 in FIG. 6A and in a second, unfolded configuration 650 in FIG. 6B.

The transducer 602 has a first transducer array 604 and a second transducer array 606. The first and second transducer arrays 604, 606 have similar dimensions, e.g., length, width, and thickness, and are each rectangular and longitudinally aligned with the x-axis, e.g., a length 608 of each transducer array is parallel with the x-axis. However, in other examples, the first and second transducer arrays 604, 606 may have different dimensions from one another. For example, the first transducer array 604 may be wider and/or longer than the second transducer array 606. A SMP 610 is arranged between the transducer arrays, along the z-axis. In other words, the first transducer array 604 is spaced away from the second transducer array 606 by a width 612 of the SMP 610, as shown in FIG. 6B. The width 612 of the SMP 610 may be less than a width 614 of each of the first and second transducer arrays 604, 606 while a length of the SMP 610, defined along the x-axis, may be similar to the length 608 of the transducer arrays.

The SMP 610 may be connected to inner edges of a backing layer 616 of each of the first and second transducer arrays 604, 606. For example, the SMP 610 may be directly in contact with and adhered to a longitudinal inner edge 618 of the backing layer 616 of the first transducer array 604, e.g., an edge of the backing layer 616 facing the second transducer array 606 and aligned with the x-axis, and to a longitudinal inner edge 620 of the backing layer 616 of the second transducer array 606, e.g., an edge of the backing layer 616 facing the first transducer array 604 and aligned with the x-axis. A thickness of the SMP 610 may be similar to a thickness of the backing layer 616 of each of the first and second transducer arrays 604, 606, the thicknesses defined along the y-axis. A matching layer 622 is stacked above the backing layer 616 of each of the transducer arrays. An element, e.g., a piezoelectric element, may be arranged between the matching layer 622 and the backing layer 616 (not shown in FIGS. 6A and 6B).

When in the first configuration 600 as shown in FIG. 6A, the SMP 610 is curved into a semi-circular shape. The second transducer array 606 is stacked directly over and aligned with the first transducer array 604, with respect to the y-axis, and spaced away from the first transducer array 604 so that both transducer arrays are maintained parallel with the x-z plane. The transducer 602 is folded in FIG. 6A so that each matching layer 622 of the transducer arrays face away outwards and away from one another and the backing layers 616 of the transducer arrays face one another. The backing layers 616 may be spaced away from one another by a distance 630 similar to a diameter of the semi-circle formed by the SMP 610. However, in other examples, the transducer 602 may be folded in an opposite direction so that the backing layers 616 of the transducer arrays face one another and the matching layers 622 face away from one another.

In the first configuration 600, a width 624 of the transducer 602 is reduced relative to a width 626 of the transducer 602 in the second configuration 650. An active area of the transducer 602 may be equal to a surface area of one of the first or second transducer arrays 604, 606. In the second configuration 650, with the first and second transducer arrays 604, 606 co-planar with one another and side-by-side, the active area of the transducer 602 is doubled relative to the first configuration 600 when the transducer arrays are similar in size. As such, an elevation aperture of the transducer 602 may be doubled when unfolded into the second configuration 650, thereby increasing a resolution and penetration of the transducer 602.

In another example, a transducer of an imaging probe may include more than two sections or transducer arrays. A second example of a transducer 702 is shown in a first, folded configuration 700 in FIGS. 7A and 7C, and a second, unfolded configuration 750 in FIG. 7B. The transducer 702 includes a first transducer array 704, a second transducer array 706, and a third transducer array 708. All three transducer arrays may have similar dimensions, e.g., length, width, and thickness, as well as geometries and may be connected by a first SMP 710 and a second SMP 712. However, in other examples, the transducer arrays may all have different dimensions from one another or two of the three transducer arrays may be similar and the remaining transducer array may have a different size or shape.

Figure 7B:
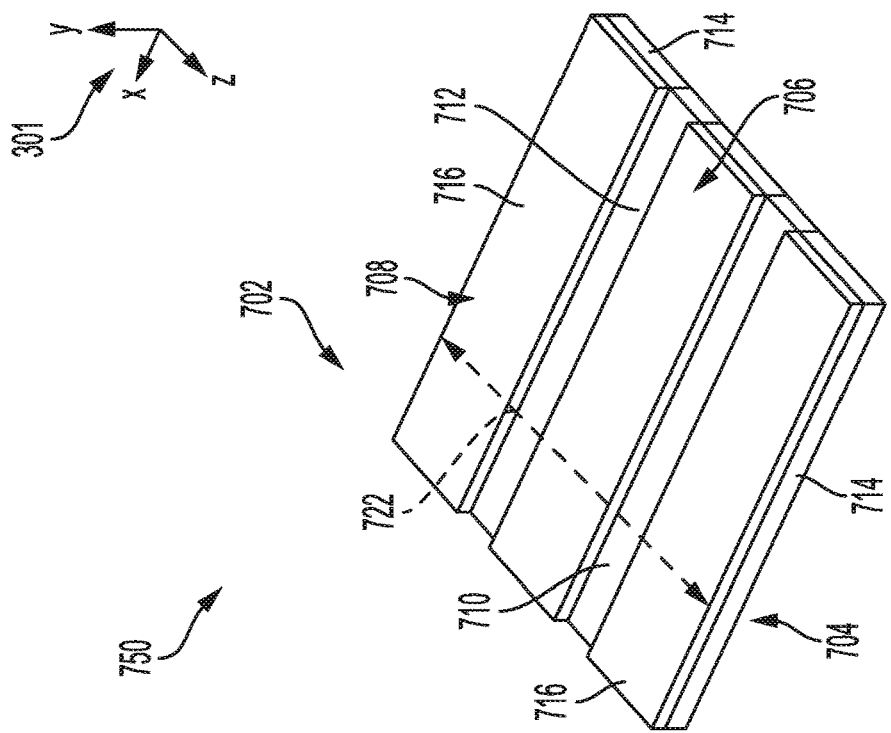
FIG. 7B shows the second example of the transducer of FIG. 7A in an unfolded configuration.

For example, the transducers may be spaced away from one another but co-planar and aligned along the x-axis and z-axis in the second configuration 750 of FIG. 7B. The first transducer array 704 is spaced away from the second transducer array 706 by the first SMP 710 and the second transducer array 706 is spaced away from the third transducer array 708 by the second SMP 712. As described above for the first example of the transducer 602 of FIGS. 6A-6B, the SMPs may be directly connected to longitudinal inner edges of the transducer arrays along a backing layer 714 of each of each of the transducer arrays. The SMPs may be co-planar and have a similar thickness to the backing layer 714 of the transducer arrays. A matching layer 716 of each of the transducer arrays is positioned above the backing layer 714 and aligned with each backing layer 714 along the y-axis. As such, the matching layer 716 protrudes above the first and second SMPs 710, 712 with respect to the y-axis. An element may be arranged between the matching layer 716 and the backing layer 714 (not shown in FIGS. 7A and 7B).

Figure 7A:
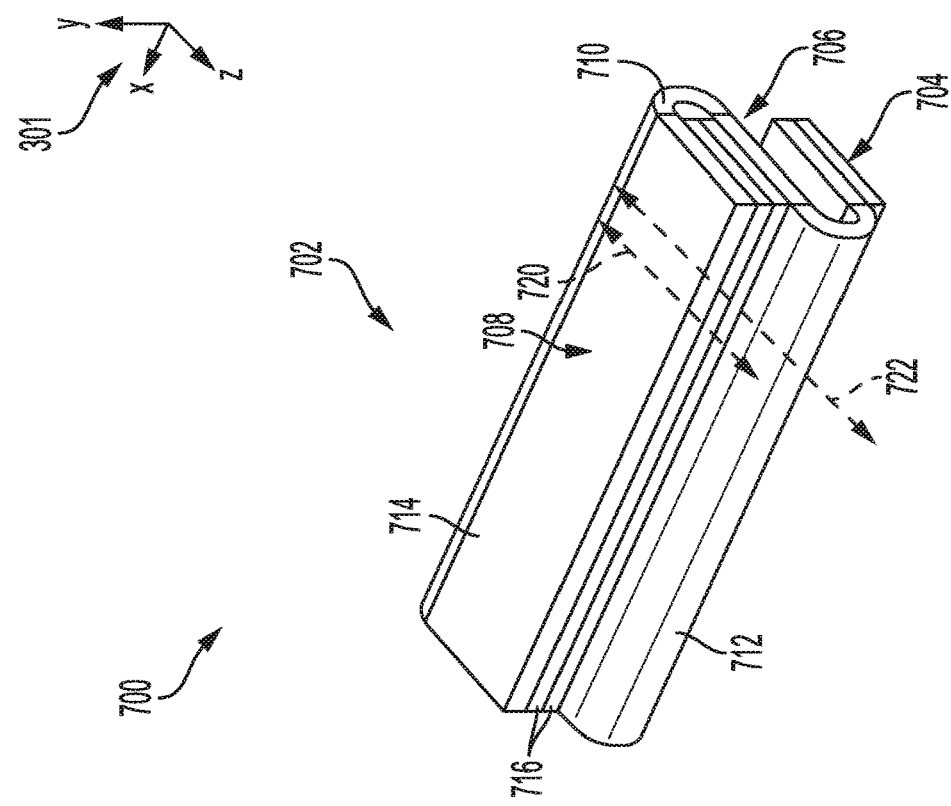
FIG. 7A shows a second example of a transducer adapted with a shape memory material in a folded configuration.

In the first configuration 700 of FIG. 7A, the transducer 702 is folded into an S-shaped geometry when viewed along the x-axis. In the S-shaped geometry, the first SMP 710 is bent into a semi-circle, forming a right half of a circle. The first transducer array 704 may be pivoted through a first rotational direction relative to the second transducer array 706 so that the second transducer array 706 is stacked over and aligned with the first transducer array 704 with respect to the y-axis. While the backing layer 714 of the second transducer array 706 and the backing layer 714 of the first transducer array 704 face each other with no other component of the transducer 702 positioned therebetween, the backing layers 714 of the transducer arrays are spaced apart by a distance similar to a diameter of the semi-circle formed by the first SMP 710.

The second SMP 712 is bent in an opposite direction from the first SMP 710, into a semi-circle forming a left half of a circle. The bending of the second SMP 712 causes the third transducer array 708 to be stacked over the second transducer array 706 along the y-axis. The third transducer array 708 is pivoted through a second rotational direction, opposite of the first rotation direction, so that the third transducer array 708 is aligned with both the first and second transducer arrays 704, 706, along the y-axis and the matching layer 716 of the third transducer array 708 faces the matching layer 716 of the second transducer array 706. The matching layers 716 of the second and third transducer arrays 706, 708 are separated by a gap that is smaller than the distance between the backing layers 714 of the first and second transducer arrays 704, 706.

A width 720, as shown in FIG. 7A, of the transducer 702 in the first configuration 700 may be narrower than a width 722 of the transducer 702 in the second configuration 750. An active area of the transducer 702, determined by a total, e.g., cumulative, transducer array surface area along the x-z plane facing a same direction, may be increased, for example, threefold when the transducer 702 is adjusted from the first configuration 700 to the second configuration 750 when the transducer arrays are of similar size. Thus, when a transducer is formed of three transducer arrays (a 3-section transducer, hereafter), and the unfolded 3-section transducer, e.g., the second configuration 750 of FIG. 7B, is equal in size to an unfolded transducer with two transducer first arrays (a 2-section transducer, hereafter), e.g., the second configuration 650 of FIG. 6B, the transducer arrays of the 3-section transducer may be narrower in width than the transducer arrays of the 2-section transducer. When folded, the 3-section transducer may have a smaller footprint than the 2-section transducer and may thereby be inserted through narrower channels.

Alternatively, the transducer arrays of the 3-section and 2-section transducers may be similar in size. When folded, both the transducers may have a similar footprint. However, when deployed and unfolded in a target scanning site, the 3-section transducer may have a larger active area, allowing the 3-section transducer to have greater resolution and penetration than the 2-section transducer. Furthermore, the first and second examples of the transducers shown in FIGS. 6A-7B are non-limiting examples. Other examples may include transducers with more than three sections, or transducers and transducer arrays with different geometries and dimensions from those shown. Thus, a transducer may be selected based on a desired footprint of the folded and/or unfolded transducer. For example, when the 3-section and 2-section transducers have a similar footprint in the folded configuration, the 3-section transducer may be used when a target imaging site with more volume than when the 2-section transducer is used.

Positioning a SMP between each transducer array of a transducer, as shown in FIGS. 6A-7B, allows the transducer to be varied in size along an elevation direction of the transducer. However, if a distance between the transducer arrays of the transducer is too large, an image quality generated by the transducer may be degraded. For example, in order to maintain the enhanced performance of a transducer provided by increasing an active area of the transducer, the distance between each transducer array of the transducer may be cumulatively no more than a threshold percentage, such as 5%, of a total active elevation aperture of the transducer. Thus, minimizing the distance between the transducer arrays during data acquisition at the transducer is desirable. However, folding of the transducer along an azimuth aperture, as shown in FIGS. 5, 6A and 7A may be a shape transition offering a lowest degree of complexity and easily initiated. To facilitate efficient packaging of the transducer by folding, a total spacing of the distances between the transducer arrays greater than the threshold percentage of the total active elevation aperture may be demanded.

In one example, the distance between transducer arrays when the transducer is unfolded may be decreased by positioning the SMP outside of the active area of the transducer. Such an arrangement is referred to as an external arrangement of the SMP hereafter. Relocating the SMP outside of the active area, along the azimuth aperture of the transducer may allow bending of the transducer to be displaced away from the transducer arrays, alleviating a demand for a minimum distance between the transducer arrays to enable sufficient bending of the SMP. A first example of a transducer 802 equipped with an externally arranged SMP is shown in FIGS. 8A-8D. The transducer 802 is depicted in FIG. 8A in a folded configuration from a perspective view 800 and in FIG. 8B from an end view 830. The transducer 802 is further illustrated in FIG. 8C in a perspective view 850 showing the transducer 802 in a transitional configuration and in FIG. 8D in a perspective view 870 of the transducer 802 in an unfolded configuration.

As shown in FIG. 8A, the transducer 802 includes a first transducer array 804, a second transducer array 806, and a SMP 808 positioned at one end of the first and second transducer arrays 804, 806 along the x-axis, which may also be an azimuth direction of the transducer 802. The transducer arrays may be aligned longitudinally with the azimuth direction and parallel with one another. The first and second transducer arrays 804, 806 are not directly coupled to one another, e.g., the transducer arrays may come into contact with one another during shape transitions but are not attached to one another at any point. Each of the transducer arrays has a matching layer 810 and a backing layer 812. The first and second transducer arrays 804, 806 may have similar widths 814 and similar lengths 816, as shown in FIG. 8A, and may both be longitudinally aligned with the x-axis and parallel with one another.

Figure 8B:
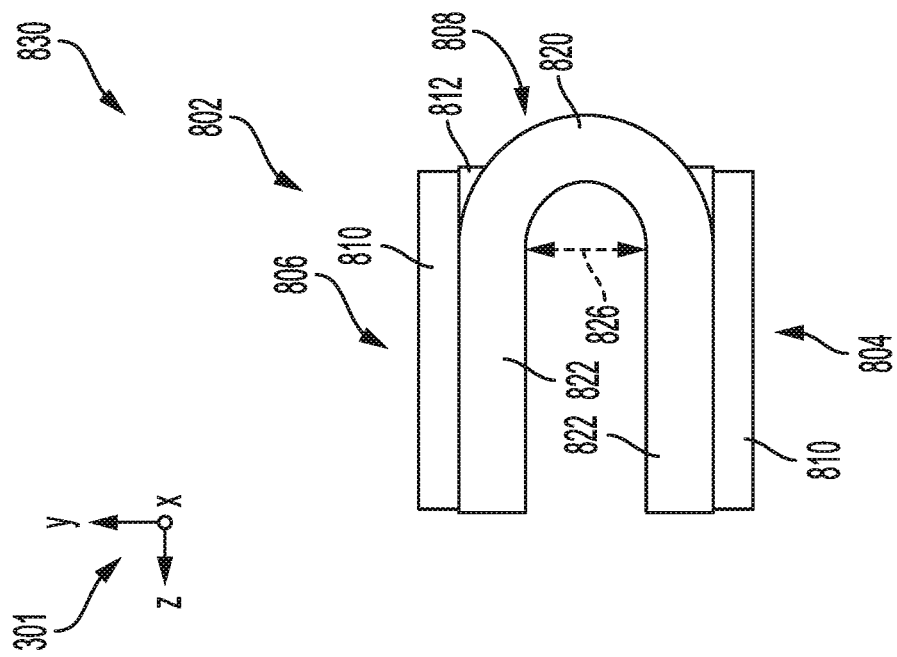
FIG. 8B shows an end view of the third example of the transducer of FIG. 8A.
Figure 8A:
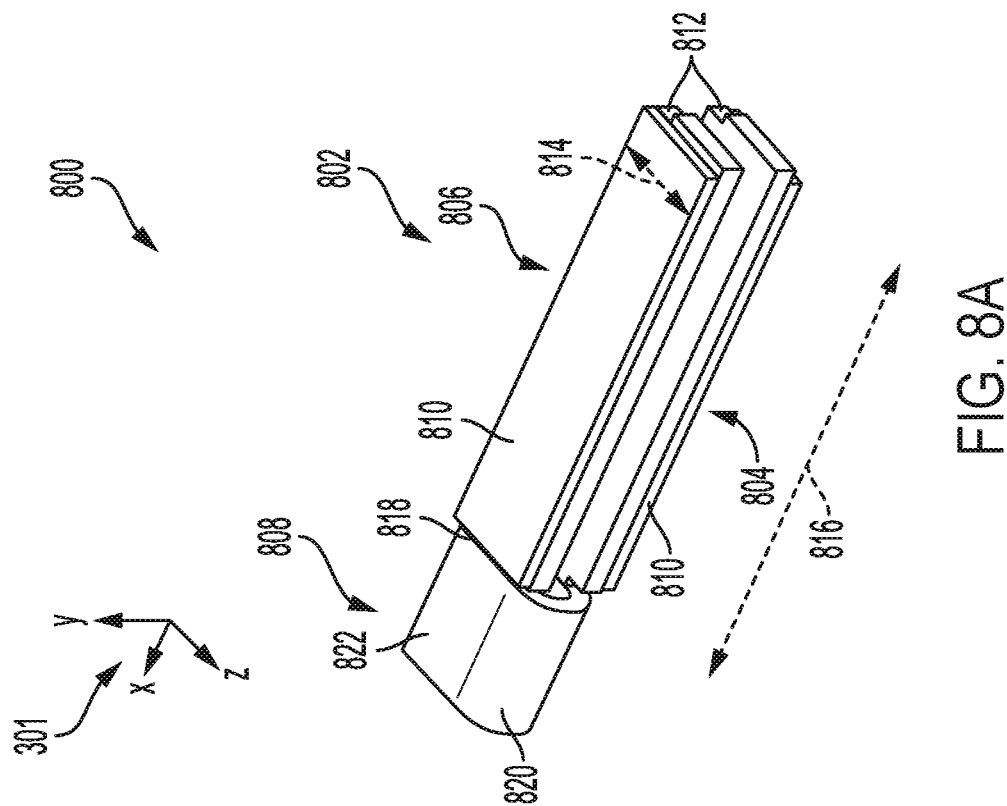
FIG. 8A shows a perspective view of a third example of a transducer adapted with a shape memory material in a folded configuration.

The SMP 808 is coupled to a first edge 818 of the backing layer 812 of each of the transducer arrays, as shown in FIGS. 8A, 8C and 8D, by an adhesive, for example. In other examples, however, when the SMP has attenuating properties, such as when the SMP is configured as a matching layer, the SMP may be a part of the transducer arrays, e.g., integrated into the transducer arrays. The first edge 818 is parallel with the z-axis and extends along the width 814 of each transducer array. A thickness of the SMP 808 may be less than a thickness of each of the transducer arrays, the thicknesses defined along the y-axis, so that the matching layers 810 protrude higher along the y-axis than the SMP 808, as shown in FIG. 8D. A central region 820 of the SMP 808 is not attached to the transducer arrays and is configured to bend as shown in FIGS. 8A, 8B, and 8C. The central region 820 is positioned between planar regions 822 of the SMP 808 which do not bend due to coupling of the planar regions 822 to the first edge 818 of the backing layer 812 of each of the transducer arrays.

In the folded configuration depicted in FIGS. 8A and 8B, the SMP 808 is bent so that the planar regions 822 are stacked over one another along the y-axis and the central region 820 forms a semi-circle. The bending of the SMP 808 causes the first transducer array 804 to fold under the second transducer array 806 to become stacked under the second transducer array 806 along the y-axis. For example, the first transducer array 804 may be pivoted, as indicated by arrow 824 shown in FIG. 8D, through 180 degrees in a first rotational direction, e.g., counterclockwise, relative to the unfolded configuration. In some examples, the first transducer array 804 may be pivoted greater than 180 degrees, such as 190 or 210 degrees, or any angle less than 180 degrees. It will be appreciated that while pivoting of the first transducer array 804 is described, in other examples, the second transducer array 806 may be pivoted instead.

When adjusted to the folded configuration, the backing layers 812 of the first transducer array 804 and the second transducer array 806 may face one another, separated by distance equal to a diameter 826 of the semicircle formed by the central region 820 of the SMP 808, as shown in FIG. 8B. In the folded configuration, an active area of the transducer 802 may be a total surface area of the transducer facing one direction. As such, the active area may be equal to an area of one of the transducer arrays.

In the folded configuration, the transducer 802 may have a sufficiently small footprint to fit within an outer housing of a deployable catheter for intravenous passage. Upon reaching a target imaging site, the transducer 802 may be expanded to the unfolded configuration shown in FIG. 8D. As the transducer 802 unfolds, a straightening of the SMP 808 causes the first transducer array 804 to be rotated in a second rotational direction, opposite of the direction indicated by arrow 824, e.g., clockwise, passing through the transitional configuration shown in FIG. 8C. The first and second transducer arrays 804, 806 are separated by a gap extending longitudinally between the transducer arrays until the transducer 802 is in the unfolded configuration of FIG. 8D.

As shown in FIG. 8D, the transducer 802 is planar, e.g., co-planar with the x-z plane, including both the first and second transducer arrays 804, 806 and the SMP 808. The central region 820 of the SMP 808 is co-planar with the planar regions 822, together forming a rectangular extension of the transducer 802 along the x-axis. A width 834 of the SMP 808 may be similar to a sum of the widths 814 of the transducer arrays and a length 832 of the SMP 808 is less than the length 816 of the transducer arrays.

The first and second transducer arrays 804, 806 may be positioned very close to one another in the unfolded configuration, e.g., the first and second transducer arrays 804, 806 are contiguous, without any other transducer components arranged in a region of space in between the transducer arrays. The region between the transducer arrays may be defined or bound by inner edges of the transducer arrays and by edges of the transducer arrays perpendicular to the azimuth direction. The transducer arrays may be separated by a small gap or, in some examples, inner edges of the backing layer 812 of each transducer array may be in contact when the transducer 802 is unfolded. The active area of the transducer 802 may be doubled relative to the folded configuration and a distance between the transducer arrays may be smaller than when the SMP is positioned between the transducer arrays. For example, the total distance between the transducer arrays may be less than 5% of the elevation aperture of the transducer 802.

An active area of a transducer may be more than doubled by adapting the transducer with more than two transducer arrays. As shown in FIGS. 9A-9D, a second example of a transducer 902, equipped with two externally arranged SMPs, may include a first transducer array 904, a second transducer array 906, and a third transducer array 908. The transducer arrays may be longitudinally aligned with the azimuth direction (e.g., the x-axis) and parallel with one another. The transducer 902 is depicted in FIG. 9A in a folded configuration from a perspective view 900 and in FIG. 9B from an end view 930. The transducer 902 is further illustrated in FIG. 9C in a perspective view 950 showing the transducer 902 in a transitional configuration and in FIG. 9D in a perspective view 970 of the transducer 902 in an unfolded configuration.

The transducer 902 may include a first SMP 910 positioned at first end 912 of the transducer 902 and a second SMP 914 positioned at a second end 916 of the transducer 902. The first and second SMPs 910, 914 may each be attached to two of the transducer arrays and may be formed of a same or different material. More specifically, the first SMP 910 is coupled to the first transducer array 904 and the second transducer array 906 at the first end 912 and the second SMP 914 is coupled to the second transducer array 906 and the third transducer array 908 at the second end 916. Each of the transducer arrays has a matching layer 918 and a backing layer 920 and may each have similar widths 922 and similar lengths 924, as shown in FIG. 9A. The transducer arrays may each be longitudinally aligned with the x-axis. A thickness of each of the first and second SMPs 910, 914 may be similar to one another and less than a thickness of each of the transducer arrays, the thicknesses defined along the y-axis, so that the matching layers 918 protrude higher along the y-axis than the SMPs in the unfolded configuration of FIG. 9D.

The second transducer array 906 is positioned between the first transducer array 904 and the third transducer array 908 and the transducer arrays are not directly coupled to one another. Instead, the transducer arrays are linked by the first and second SMPs 910, 914 and transitioning of the transducer 902 between the folded and unfolded configurations are guided by the SMPs. Each of the SMPs includes a central region 926 configured to flex, and planar regions 928 arranged on opposite sides of the central region 926. The planar regions 928 are in edge-sharing contact with edges of the backing layers 920 of the transducer arrays and fixedly coupled to the edges of the backing layers 920.

When adjusted to the folded configuration shown in FIGS. 9A and 9B, the first SMP 910 may bend so that the first transducer array 904 is pivoted through, for example, 180 degrees in a first rotational direction, relative to the unfolded configuration of FIG. 9D, to become stacked below the second transducer array 906 along the y-axis. The second SMP 914 may bend in an opposite direction from the first SMP 910 so that the third transducer array 908 is pivoted through, for example, 180 degrees in a second rotational direction, opposite of the first rotational direction, to become stacked above the second transducer array 906 along the y-axis. As described above, other examples may include rotation of the first and third transducer arrays 904, 908 through more or less than 180 degrees. Furthermore, in other examples, the transducer 902 may be folded in an opposite configuration, e.g., the first transducer array 904 over the second transducer array 906 and the third transducer array 908 under the second transducer array 906. In the folded configuration, the stacked transducer arrays are aligned along the y-axis but spaced apart from one another, as shown in FIG. 9B.

The end view 930 of FIG. 9B shows an S-shaped geometry of the transducer. The backing layers 920 of the first and second transducer arrays 904, 906 face one another in the folded configuration while the matching layers 918 of the second and third transducer arrays 906, 908 face one another. The first and second transducer arrays 904, 906 are spaced apart by a distance similar to a diameter 932 of the semi-circle formed by the first SMP 910. The second and third transducer arrays 906, 908 are spaced apart by a distance that is smaller than a diameter of the semi-circle formed by the second SMP 914. The transducer arrays are therefore not in contact with one another when the transducer 902 is in the folded configuration.

When the transducer transitions from the folded configuration to the unfolded configuration, the first SMP 910 may straighten, causing the first transducer array 904 to be pivoted through the second rotational direction as indicated by arrow 934 in FIG. 9B. The second SMP 914 may also straighten, swinging the third transducer array 908 along the first rotational direction, as indicated by arrow 936 in FIG. 9B. The transducer 902 may pass through the transitional configuration shown in FIG. 9C with the transducer arrays still spaced apart and not in contact with one another.

The first and second SMPs 910, 914 become aligned with the x-z plane, e.g., flat, in the unfolded configuration shown in FIG. 9D. The SMPs form rectangular extensions along the x-axis at opposing sides of the transducer 902 and may be offset from one another along the x-axis. For example, the first SMP 910 has a width 972 similar or slightly greater than the combined widths 922 of the first and second transducer arrays 904, 906 and is positioned at the first end 912 of the transducer 902. The second SMP 914 has a width 974 similar or slightly greater than the combined widths 922 of the second and third transducer arrays 906, 908 and is positioned at the second end 916 of the transducer 902. The second SMP 914 is positioned higher than the first SMP 910 with respect to the z-axis.

In the unfolded configuration, the transducer arrays are aligned along the x, y, and z-axes and co-planar with one another along a common plane. The transducer arrays are depicted spaced away from one another by a small gap which is less than a distancing of the transducer arrays when the SMPs are instead arranged between the transducer arrays. In some examples, the transducer arrays may be in edge-sharing contact in the unfolded configuration, e.g., inner edges of the transducer arrays are in contact with one another. As described above for the transducer 802 shown in FIGS. 8A-8D, the first, second, and third transducer arrays 904, 906, and 908 are arranged contiguously when the transducer 902 is unfolded, without any other transducer components arranged in regions of space in between the transducer arrays. The regions between the transducer areas may be defined or bound by inner edges of the transducer arrays and by edges of the transducer arrays perpendicular to the azimuth direction.

An active area of the transducer 902 may be tripled when the transducer 902 is unfolded relative to when the transducer is folded when the transducer arrays are similar in size. By placing the SMPs outside of the active area, the transducer arrays are positioned closer together and a total distance between the transducer arrays may thereby be less than 5% of an elevation aperture of the transducer. The external arrangement of the SMP may allow the distance between the transducer arrays to be reduced without introducing additional complexity to a shape transition of the SMP or to a manufacturing process of the transducer. The SMP may be arranged external to the active area of the transducer when packaging space along the azimuth direction of the transducer is not constrained.

As shown in FIGS. 5-9D, a SMP may be attached to a backing layer of a transducer, e.g., to individual backing layers of each transducer array of the transducer. Alternatively, the SMP may be similarly coupled to a matching layer of each transducer array, in some examples. The material of the SMP may be selected to be physically compatible with a material of the backing layer to reduce a likelihood of separation between the SMP and the matching layer or backing layer during transitioning of the SMP between shapes. A fabrication and material selection may be simplified, however, by incorporating the SMP as an acoustic layer of the transducer. As such, the SMP may form either the backing layer or the matching of the transducer, as shown in FIGS. 10-11.

FIG. 10 shows a first example of a transducer 1000 with a SMP forming an acoustic layer. The transducer 1000 has a first transducer array 1002 and a second transducer array 1004, spaced away from one another along the x-axis. A SMP 1006 extends between the transducer arrays and across an entire width 1008 of the transducer 1000, forming a continuous backing layer across the transducer 1000. Thus, each transducer array is coupled to a common backing layer and remaining components, e.g., a matching layer 1010 and an element 1012, of an acoustic stack of each transducer array may be laminated onto the SMP 1006. The transducer 1000 may be diced downwards, with respect to the y-axis, from a top of the matching layer 1010, through the element 1012 to a top of the SMP 1006. When forming the backing layer of the transducer 1000, the SMP 1006 may include an additive to lend the SMP 1006 attenuating properties. For example, the SMP 1006 may have an increased density and/or include silicone and tungsten as additives.

Alternatively, a SMP may form a matching layer of a transducer. A second example of a transducer 1100 is shown in FIG. 11 with a SMP 1102 forming a continuous matching layer extending entirely across a width 1104 of the transducer 1100. The transducer 1100 has a first transducer array 1106 and a second transducer array 1108. The transducer arrays are spaced apart from one another along the x-axis with the SMP 1102 extending between the transducer arrays. The transducer 1100 may be diced upwards, with respect to the y-axis, from a bottom of a backing layer 1110, through an element 1112, to a bottom of the SMP 1102. When forming the matching layer of the transducer 1100, the SMP 1102 may be formed of a base polymer.

By implementing a SMP as an acoustic layer of a transducer, rather than as a linkage between transducer arrays of the transducer, an adhering of the SMP to a backing layer (or matching layer) of the transducer arrays is precluded. Thus fewer materials and components are demanded of a manufacturing process, thereby decreasing costs. Furthermore, shape-changing properties provided by the SMP are incorporated into the transducer without adding thickness to the transducers. A thickness, and a footprint of the transducer is maintained, e.g., not increased, while enhancing transducer gain.

As described above, a performance of a transducer with transducer arrays spaced apart by a SMP extending between the transducer arrays, whether the SMP forms sections between the transducer arrays, as shown in FIGS. 6A-7B, or forms a continuous, common acoustic layer of the transducer arrays, as shown in FIGS. 10-11, may be hindered by a distancing separating the transducer arrays from one another. Positioning of the SMP external to the active area may be precluded as a result of limited packaging space along an azimuth direction of the transducer. A minimum cumulative distance between the transducer arrays that is greater than threshold amount (e.g., 5% of an elevation aperture), however, may be demanded to allow the SMP to bend and fold the transducer into a folded configuration. This issue may be at least partially addressed by configuring the SMP to change shape via more than one transition path. For example, the SMP may fold, in response to a first stimulus, and contract along at least one dimension, in response to a second stimulus.

The SMP may have a large deformation capability of, for example, up to 800%. By using an SMP adapted to contract along at least one dimension in response to a stimulus, the distance between transducers may be decreased. As an example, as shown in FIG. 12 in a second diagram 1200, a transducer 1250 has a first transducer array 1202 and a second transducer array 1204 spaced apart from the first transducer array 1202 by a SMP 1206. The transducer 1250 is depicted in a first, folded configuration 1201, where an active area of the transducer 1250 is reduced relative to a second, unfolded configuration 1203.

Upon exposure to a first stimulus, $S_1$, the SMP 1206 transitions to the second configuration 1203. The first stimulus $S_1$ may be any of the stimuli described above. An active area of the transducer 1250, e.g., a total surface area of the transducer 1250 facing a same direction along the y-axis, is doubled relative to the first configuration 1201. The first transducer array 1202 is spaced away from the second transducer array 1204 by the SMP 1206 which has a first width 1208 in the second configuration 1203, the width defined along the x-axis which may also be an elevation direction of the transducer 1250.

The SMP 1206 may be exposed to a second stimulus $S_2$, different from the first stimulus $S_1$, which may compel the SMP 1206 to shrink along the x-axis. In one example, the first stimulus $S_1$ may be temperature and the second stimulus $S_2$ may be humidity. In other examples, the first and second stimuli $S_1$, $S_2$ may be any combination of various chemical, physical, and biological stimuli. A contraction of the SMP 1206 along the elevation direction transitions the transducer 1250 into a third, contracted configuration 1205. In the third configuration 1205, the SMP 1206 has a second width 1210 which is smaller than the first width 1208. The distance between the first and second transducer arrays 1202, 1204 is thus reduced. The transducer 1250 may transition from the third configuration 1205 to the second configuration 1203 and from the second configuration 1203 to the first configuration 1201 by exposing the SMP 1206 to more than one stimulus. The SMP 1206 may be similarly applied to transducers with more than two transducer arrays, such as the transducer 902 of FIGS. 9A-9D.

To return the transducer 1250 to the first configuration 1201, the transducer 1250 may be exposed to a variation of the second stimulus $S_2$ to expand the SMP 1206 along the x-axis. For example, if the second stimulus $S_2$ is pH, the SMP 1206 may be subjected to a first, lower pH to induce contraction and a second, higher pH to facilitate expansion. The transducer 1250 may then be exposed to a variation of the first stimulus $S_1$ to induce bending of the SMP 1206 to fold the transducer 1250. For example, if the first stimulus $S_1$ is humidity, the transducer 1250 may be exposed to a lower humidity to compel bending of the SMP 1206 and higher humidity to trigger straightening of the SMP 1206.

The contracting and expanding of the SMP 1206 allows the spacing between transducer arrays to be adjusted based on response of the SMP 1206 to stimuli. When the SMP 1206 is configured as sections arranged between the transducer arrays and coupled to inner edges of the transducer arrays, as shown in FIGS. 6A-7B, the entire section of the SMP may contract and expand. However, when the SMP 1206 forms a continuous, common acoustic layer of the transducer, as shown in FIGS. 10-11, the SMP 1206 may be adapted to contract and expand only in regions extending between the transducer arrays, e.g., region 1050 indicated in FIGS. 10 and 11. Furthermore, the SMP 1206 may, in some examples, be configured to contract and expand along the azimuth direction in addition to or instead of the elevation direction. By constraining the region of contraction and expansion, undesirable separation of the SMP from transducer components coupled to the SMP may be mitigated.

It will be appreciated that the examples of shape transitions described above, e.g, bending and contracting, are non-limiting examples. Various other modes of shape change have been contemplated for use in a deployable catheter. For example, in addition to bending and contracting, the SMP may curl, twist, and/or expand. The SMP may be configured to change shape via more than more mode depending on an applied stimulus and a desired level of complexity.

In this way, a transducer for a deployable catheter may readily pass intravenously through a patient and provide images with enhanced field of view, resolution, penetration, and image update rate. Transducer arrays of the transducer may be linked to one another by a SMP and the transducer may transition between at least a first, folded shape and a second, unfolded shape as a result of a response of SMP to stimuli. An active area of the transducer may be selectively increased, enhancing a performance of the transducer. The SMP may be incorporated in the transducer via more than one configuration. For example, the SMP may be attached to edges of the transducer arrays and extend between the transducer arrays. Alternatively, the SMP may form a continuous, common acoustic layer of the transducer arrays and bend at regions between the transducer arrays. In order to decrease a distance between the transducer arrays during data acquisition, the SMP may be configured to contract along at least one dimension. Furthermore, when packaging space is available along an azimuth aperture of the transducer, the SMP may be located outside of the active area of the transducer, also resulting in a decrease in the distance between the transducer arrays. As such, a data quality and speed of data acquisition of the transducer may be increased at low cost while allowing the transducer to be adjusted to a conformation favorable for intravenous passage of the deployable catheter.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The disclosure also provides support for a deployable invasive device comprising: a transducer with a plurality of transducer arrays linked by at least one shape memory material, the at least one shape memory material configured to transition the transducer between a first, folded shape and a second, unfolded shape in response to one or more stimuli, wherein in the second, unfolded shape, the plurality of transducer arrays are arranged contiguously with one another without any other transducer components positioned in a region between each of the plurality of transducer arrays, the region defined by inner edges of the plurality of transducer arrays and edges of the plurality of transducer arrays perpendicular to an azimuth direction, and an active area of the transducer is increased relative to the first, folded shape. In a first example of the system, the at least one shape memory material is a two-way shape memory polymer. In a second example of the system, optionally including the first example, the at least one shape memory material is positioned along one side of the transducer along the azimuth direction and extending between an edge of each of the plurality of transducer arrays perpendicular to the azimuth direction. In a third example of the system, optionally including the first and second examples, the at least one shape memory material is coupled to the edge of each of the plurality of transducer arrays at planar sections of the at least one shape memory material and wherein the planar sections are spaced apart from one another by a central section of the at least one shape memory material. In a fourth example of the system, optionally including the first through third examples, the central section of the at least one shape memory material is not coupled to the plurality of transducer arrays and wherein the central section of the at least one shape memory material is configured to transition between a bent geometry when the transducer is in the first, folded shape and a less bent geometry when the transducer is in the second, unfolded shape. In a fifth example of the system, optionally including the first through fourth examples, the plurality of transducer arrays includes a first transducer array and a second transducer array, each of the first transducer array and the second transducer array coupled to the at least one shape memory material along an edge perpendicular to the azimuth direction at a same side of the transducer. In a sixth example of the system, optionally including the first through fifth examples, the plurality of transducer arrays includes a first transducer array, a second transducer array, and a third transducer array, the second transducer array positioned between the first and the third transducer arrays, and wherein the at least one shape memory material includes a first shape memory material coupled to edges of the first and the second transducer arrays perpendicular to the azimuth direction at a first side of the transducer and a second shape memory material coupled to edges of the second and the third transducer arrays perpendicular to the azimuth direction at a second side of the transducer, the second side opposite of the first side. In a seventh example of the system, optionally including the first through sixth examples, at least one transducer array is pivoted relative to an adjacent transducer array along a first rotational direction when the transducer is transitioned from the first, folded shape to the second, unfolded shape and wherein the at least one transducer array is more co-planar with the adjacent transducer array in the second, unfolded shape than in the first, folded shape. In an eighth example of the system, optionally including the first through seventh examples, the at least one transducer array is pivoted in a second rotational direction, opposite of the first rotational direction when the at least one transducer is transitioned from the second, unfolded shape to the first, folded shape and wherein the at least one transducer array is aligned and parallel with the adjacent transducer array along a vertical axis of the transducer in the first, folded shape.

The disclosure also provides support for a transducer for an imaging catheter comprising: two or more transducer arrays linked by a shape memory polymer (SMP) configured to undergo one or more shape transitions to adjust an active area of the transducer, the active area a cumulative surface area of the two or more transducer arrays facing a same direction, and a distance between each of the two or more transducer arrays. In a first example of the system, the one or more shape transitions includes a bending of the SMP into a curved shape and unbending of the SMP into a planar geometry. In a second example of the system, optionally including the first example, the transducer is adjusted to a folded configuration when the SMP is bent into the curved shape and to an unfolded configuration when the SMP is unbent into the planar geometry and wherein the active area of the transducer is larger in the unfolded configuration than in the folded configuration. In a third example of the system, optionally including the first and second examples, the active area is increased at least 1.5 times in the unfolded configuration relative to the folded configuration of the transducer. In a fourth example of the system, optionally including the first through third examples, the one or more shape transitions includes a contraction and expansion of the SMP at least in regions of the SMP extending between the two or more transducer arrays and wherein the contraction and expansions occurs along an elevation aperture of the transducer. In a fifth example of the system, optionally including the first through fourth examples, the contraction and expansion of the SMP is triggered by exposure of the SMP to one or more stimuli when the active area of the transducer is increased. In a sixth example of the system, optionally including the first through fifth examples, the SMP is positioned as sections coupled to and extending between inner edges of the two or more transducer arrays. In a seventh example of the system, optionally including the first through sixth examples, the SMP is configured as a continuous layer across the entire transducer and forms one of a common matching layer or a common backing layer of the two or more transducer arrays. In an eighth example of the system, optionally including the first through seventh examples, each of the one or more shape transitions are induced by different stimuli and the different stimuli includes any of chemical, physical and biological stimuli.

The disclosure also provides support for a transducer for a deployable catheter, comprising: two or more transducer arrays linked by a shape memory polymer (SMP) configured to contract and expand along an elevation and/or an azimuth aperture of the transducer in regions of the SMP extending between each of the two or more transducer arrays. In a first example of the system, a cumulative width of the SMP is 5% or less of the elevation and/or the azimuth aperture of the transducer when the SMP contracts.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A deployable invasive device comprising:
a transducer with a plurality of transducer arrays linked by at least one shape memory material, each of the plurality of transducer arrays having a backing material on one side, the at least one shape memory material comprising a shape memory polymer configured to transition in shape in response to one or more external stimuli and coupled to an edge of each of the plurality of transducer arrays, the at least one shape memory material extending away from each of the plurality of transducer arrays when the transducer is in each of a first, folded shape and a second, unfolded shape, and the at least one shape memory material configured to transition the transducer between the first, folded shape and the second, unfolded shape in response to the one or more external stimuli;
wherein in the second, unfolded shape, the plurality of transducer arrays are arranged substantially co-planar with one another and with the at least one shape memory material positioned in a region between the backing material of each of a pair of the plurality of transducer arrays, the region defined by inward facing opposing edges of the backing material of each of the pair of the plurality of transducer arrays and the region comprising the at least one shape memory material being substantially co-planar with the backing material of each of the pair of the plurality of transducer arrays extending therefrom, and an active area of the transducer is increased relative to the first, folded shape.

2. The deployable invasive device of claim 1, wherein the at least one shape memory material is a two-way shape memory polymer.

3. The deployable invasive device of claim 1, wherein the plurality of transducer arrays includes a first transducer array and a second transducer array, each of the first transducer array and the second transducer array coupled to the at least one shape memory material along an edge perpendicular to an azimuth direction at a same side of the transducer.

4. The deployable invasive device of claim 1, wherein the plurality of transducer arrays includes a first transducer array, a second transducer array, and a third transducer array, the second transducer array positioned between the first and the third transducer arrays, and wherein the at least one shape memory material includes a first shape memory material coupled to the inward facing opposing edges of the first and the second transducer arrays perpendicular to an azimuth direction at a first side of the transducer and a second shape memory material coupled to the inward facing opposing edges of the second and the third transducer arrays perpendicular to the azimuth direction at a second side of the transducer, the second side opposite of the first side.

5. The deployable invasive device of claim 1, wherein the at least one shape memory material is positioned along one side of the transducer along an azimuth direction and extending between the edge of each of the plurality of transducer arrays perpendicular to the azimuth direction.

6. The deployable invasive device of claim 5, wherein the at least one shape memory material is coupled to the edge of each of the plurality of transducer arrays at planar sections of the at least one shape memory material and wherein the planar sections are spaced apart from one another by a central section of the at least one shape memory material.

7. The deployable invasive device of claim 6, wherein the central section of the at least one shape memory material is not coupled to the plurality of transducer arrays and wherein the central section of the at least one shape memory material is configured to transition between a bent geometry when the transducer is in the first, folded shape and a less bent geometry when the transducer is in the second, unfolded shape.

8. The deployable invasive device of claim 1, wherein at least one transducer array is pivoted relative to an adjacent transducer array along a first rotational direction when the transducer is transitioned from the first, folded shape to the second, unfolded shape and wherein the at least one transducer array is more co-planar with the adjacent transducer array in the second, unfolded shape than in the first, folded shape.

9. The deployable invasive device of claim 8, wherein the at least one transducer array is pivoted in a second rotational direction, opposite of the first rotational direction when the at least one transducer is transitioned from the second, unfolded shape to the first, folded shape and wherein the at least one transducer array is aligned and parallel with the adjacent transducer along a vertical axis of the transducer in the first, folded shape.

10. The deployable invasive device of claim 1, wherein the plurality of transducer arrays includes a first transducer array having a first backing material attached thereto, a second transducer array having a second backing material attached thereto, and a first shape memory polymer comprising the at least one shape memory material, wherein the first backing material is contiguous with a first side of the first shape memory polymer, and a second side of the first shape memory polymer opposite the first side of the first shape memory polymer is contiguous with the second backing material.

11. The deployable invasive device of claim 10, wherein in the second, unfolded shape, the first backing material, the first shape memory polymer, and the second backing material are arranged substantially co-planar with one another, with the first backing material contacting the first side of the first shape memory polymer, and the second backing material contacting the second side of the first memory polymer.

12. The deployable invasive device of claim 10, wherein in the second, unfolded shape, the first backing material and the second backing material are separated from one another with the first shape memory polymer positioned therebetween.

* * * * *